(12) United States Patent
Trzecieski

(10) Patent No.: US 11,065,402 B2
(45) Date of Patent: Jul. 20, 2021

(54) AROMATHERAPY VAPORIZATION DEVICE

(71) Applicant: GSEH Holistic, Inc., Vancouver (CA)

(72) Inventor: Michael Alexander Trzecieski, Toronto (CA)

(73) Assignee: GSEH Holistic, Inc., Vancouver (CA)

( * ) Notice: Subject to any disclaimer, the term of this patent is extended or adjusted under 35 U.S.C. 154(b) by 386 days.

(21) Appl. No.: 16/009,259

(22) Filed: Jun. 15, 2018

(65) Prior Publication Data

US 2018/0289906 A1 Oct. 11, 2018

Related U.S. Application Data

(63) Continuation-in-part of application No. 14/614,005, filed on Feb. 4, 2015, now abandoned, and a (Continued)

(51) Int. Cl.
*A24F 47/00* (2020.01)
*H05B 1/02* (2006.01)
(Continued)

(52) U.S. Cl.
CPC ...... *A61M 15/0041* (2014.02); *A61M 11/044* (2014.02); *A61M 15/0035* (2014.02);
(Continued)

(58) Field of Classification Search
CPC ..... H05B 1/202; H05B 6/6458; A24F 47/008; A61M 15/00; H01S 2302/00;
(Continued)

(56) References Cited

U.S. PATENT DOCUMENTS 3,513,859 A 5/1970 Carty
3,707,017 A 12/1972 Paquette
(Continued)

FOREIGN PATENT DOCUMENTS

EP 2253233 A1 11/2010
WO 2009027959 A1 3/2009
(Continued)

OTHER PUBLICATIONS

Document relating to U.S. Appl. No. 14/614,005 dated May 17, 2018 (Office Action).
(Continued)

*Primary Examiner* — Michael A Laflame, Jr.
(74) *Attorney, Agent, or Firm* — Bereskin & Parr LLP/S.E.N.C.R.L., s.r.l.

(57) ABSTRACT

A vaporization device includes a housing, a fluid pathway extending through the housing, a heating chamber with a heating element proximate a first housing end, a control circuit and a battery disposed within the housing. The heating chamber is in fluid communication with the fluid pathway. The first chamber end is open and the second chamber end includes a closed end with one or more vents. The heating element is operable to generate heat at a predetermined vaporization temperature. The control circuit has a switch operable to control a flow of current from the battery to the heating element. In use, the predetermined vaporization temperature is sufficient to vaporize phyto material in contact with the heat at the predetermined vaporization temperature to emit a vapor. Inhaling from the second housing end draws mixed vapor and air through the fluid pathway.

19 Claims, 8 Drawing Sheets

Related U.S. Application Data continuation-in-part of application No. 14/829,660, filed on Aug. 19, 2015, now Pat. No. 10,238,764.

(60) Provisional application No. 61/935,349, filed on Feb. 4, 2014, provisional application No. 62/038,863, filed on Aug. 19, 2014, provisional application No. 62/519,972, filed on Jun. 15, 2017.

(51) Int. Cl.
  *A61M 15/00* (2006.01)
  *A61M 15/08* (2006.01)
  *A61M 11/04* (2006.01)

(52) U.S. Cl.
  CPC ......... *A61M 15/08* (2013.01); *A61M 15/0086* (2013.01); *A61M 2202/0468* (2013.01); *A61M 2205/3368* (2013.01); *A61M 2205/8206* (2013.01)

(58) Field of Classification Search
  CPC ............. H01S 3/06708; H01S 3/06733; H01S 3/06754; H01S 3/08059; H01S 3/094003; H01S 3/161; H01S 3/1608; H01S 3/0941; H01S 3/105; H01S 3/1053; H01S 3/1055; H01S 3/1603; H01S 3/302; H01S 5/0028; H01S 5/02284; H01S 5/06; H01S 5/0607; H01S 5/0612; H01S 5/06804; H01S 5/06837; H01S 5/10; H01S 5/18366; H01S 5/18369; H01S 5/4012; H01S 3/06751
  See application file for complete search history.

(56) References Cited

U.S. PATENT DOCUMENTS

| | | |
|---|---|---|
| 4,774,970 A | 10/1988 | Bell |
| 5,144,962 A | 9/1992 | Counts et al. |
| 5,261,601 A | 11/1993 | Ross et al. |
| 5,269,327 A | 12/1993 | Counts et al. |
| 5,273,190 A | 12/1993 | Lund |
| 5,591,368 A | 1/1997 | Fleischhauer et al. |
| 5,865,185 A | 2/1999 | Collins et al. |
| 6,125,853 A | 10/2000 | Susa et al. |
| 6,446,426 B1 | 9/2002 | Sweeney et al. |
| 6,513,524 B1 | 2/2003 | Storz |
| 6,761,164 B2 | 7/2004 | Amirpour et al. |
| 6,772,756 B2 | 8/2004 | Shayan |
| 6,810,883 B2 | 11/2004 | Felter et al. |
| 6,990,978 B2 | 1/2006 | Shayan |
| 7,088,914 B2 | 8/2006 | Whittle et al. |
| 7,100,618 B2 | 9/2006 | Dominguez |
| 7,141,215 B2 | 11/2006 | Guan et al. |
| 7,186,958 B1 | 3/2007 | Nelson |
| 7,434,584 B2 | 10/2008 | Steinberg |
| 7,445,007 B2 | 11/2008 | Balch et al. |
| 7,475,684 B2 | 1/2009 | Balch et al. |
| 7,624,734 B2 | 12/2009 | Balch et al. |
| 7,665,460 B2 | 2/2010 | Lindsay et al. |
| 7,726,308 B1 | 6/2010 | Flora |
| 7,826,726 B2 | 11/2010 | McCoy |
| 8,371,310 B2 | 2/2013 | Brenneise |
| 8,387,612 B2 | 3/2013 | Damani et al. |
| 8,483,552 B2 | 7/2013 | Durisek |
| 8,488,952 B2 | 7/2013 | Landry |
| 8,517,010 B2 | 8/2013 | Power et al. |
| 8,550,091 B2 | 10/2013 | Yomtov et al. |
| 8,739,786 B2 | 6/2014 | Postma |
| 8,781,306 B2 | 7/2014 | Hatten |
| 8,863,752 B2 | 10/2014 | Hon |
| 8,869,792 B1 | 10/2014 | Lee |
| 8,881,737 B2 | 11/2014 | Collett et al. |
| 8,899,230 B2 | 12/2014 | Immel |
| 8,910,630 B2 | 12/2014 | Todd |
| 8,991,402 B2 | 3/2015 | Bowen et al. |
| 10,238,764 B2 | 3/2019 | Trzecieski |
| 10,420,376 B2 * | 9/2019 | Qiu ........................ F22B 1/284 |
| 2003/0154991 A1 | 8/2003 | Fournier et al. |
| 2003/0196661 A1 | 10/2003 | Miekka et al. |
| 2005/0261641 A1 | 11/2005 | Warchol et al. |
| 2006/0054165 A1 | 3/2006 | Hughes et al. |
| 2006/0102175 A1 | 5/2006 | Nelson |
| 2006/0175425 A1 | 8/2006 | McGee et al. |
| 2006/0283449 A1 | 12/2006 | Balch et al. |
| 2007/0045288 A1 | 3/2007 | Nelson |
| 2007/0068523 A1 | 3/2007 | Fishman |
| 2007/0102013 A1 | 5/2007 | Adams et al. |
| 2007/0125765 A1 | 6/2007 | Nelson |
| 2007/0175476 A1 | 8/2007 | Lipowicz |
| 2007/0240706 A1 | 10/2007 | Kobayashi et al. |
| 2007/0280652 A1 | 12/2007 | Williams |
| 2008/0023003 A1 | 1/2008 | Rosenthal |
| 2008/0105253 A1* | 5/2008 | Pearson ............ A61M 15/0025 128/200.14 |
| 2008/0149118 A1 | 6/2008 | Oglesby et al. |
| 2009/0078253 A1 | 3/2009 | Bao |
| 2009/0126745 A1* | 5/2009 | Hon ........................ H05B 3/06 131/273 |
| 2009/0283103 A1 | 11/2009 | Nielsen et al. |
| 2009/0293892 A1 | 12/2009 | Williams et al. |
| 2009/0302019 A1 | 12/2009 | Selenski et al. |
| 2009/0320863 A1 | 12/2009 | Fernando et al. |
| 2010/0006113 A1 | 1/2010 | Urtsev et al. |
| 2010/0012118 A1 | 1/2010 | Storz |
| 2010/0074603 A1 | 3/2010 | Balch et al. |
| 2010/0119606 A1 | 5/2010 | Whittle et al. |
| 2010/0126516 A1 | 5/2010 | Yomtov et al. |
| 2010/0200006 A1 | 8/2010 | Robinson et al. |
| 2010/0322599 A1 | 12/2010 | Landry |
| 2011/0005535 A1 | 1/2011 | Xiu |
| 2011/0036346 A1 | 2/2011 | Cohen et al. |
| 2011/0041840 A1 | 2/2011 | Dunne |
| 2011/0094523 A1 | 4/2011 | Thorens et al. |
| 2011/0126831 A1 | 6/2011 | Fernandez Pernia |
| 2011/0226236 A1* | 9/2011 | Buchberger ....... A61M 15/0086 128/200.23 |
| 2011/0226266 A1 | 9/2011 | Tao |
| 2011/0236002 A1 | 9/2011 | Oglesby et al. |
| 2011/0277761 A1 | 11/2011 | Terry et al. |
| 2011/0278189 A1 | 11/2011 | Terry et al. |
| 2011/0290269 A1 | 12/2011 | Shimizu |
| 2011/0297166 A1 | 12/2011 | Takeuchi et al. |
| 2012/0037154 A1 | 2/2012 | Gallem et al. |
| 2012/0070134 A1 | 3/2012 | Durisek |
| 2012/0077849 A1 | 3/2012 | Howson et al. |
| 2012/0085344 A1 | 4/2012 | Luber et al. |
| 2012/0111347 A1* | 5/2012 | Hon ........................ H05B 3/06 131/329 |
| 2012/0199663 A1 | 8/2012 | Qiu |
| 2012/0204889 A1 | 8/2012 | Xiu |
| 2012/0234821 A1 | 9/2012 | Shimizu |
| 2012/0255546 A1 | 10/2012 | Goetz et al. |
| 2012/0255567 A1 | 10/2012 | Rose et al. |
| 2012/0269497 A1 | 10/2012 | Flatten |
| 2012/0304990 A1 | 12/2012 | Todd |
| 2012/0318882 A1 | 12/2012 | Abehasera |
| 2012/0325227 A1 | 12/2012 | Robinson et al. |
| 2013/0037041 A1 | 2/2013 | Worm et al. |
| 2013/0042865 A1 | 2/2013 | Monsees et al. |
| 2013/0087144 A1 | 4/2013 | Todd |
| 2013/0139813 A1 | 6/2013 | Storz |
| 2013/0152922 A1 | 6/2013 | Benassayag et al. |
| 2013/0167853 A1 | 7/2013 | Liu |
| 2013/0174842 A1 | 7/2013 | Young et al. |
| 2013/0206154 A1 | 8/2013 | Fernando et al. |
| 2013/0233309 A1 | 9/2013 | Todd |
| 2013/0247910 A1 | 9/2013 | Postma |
| 2013/0251354 A1 | 9/2013 | Durisek |
| 2013/0298905 A1 | 11/2013 | Levin et al. |
| 2013/0319435 A1 | 12/2013 | Flick |
| 2014/0014125 A1 | 1/2014 | Fernando et al. |
| 2014/0041655 A1 | 2/2014 | Barron et al. |

(56) References Cited

U.S. PATENT DOCUMENTS

| | | | |
|---|---|---|---|
| 2014/0064713 A1 | 3/2014 | Niemiec et al. | |
| 2014/0069424 A1 | 3/2014 | Poston et al. | |
| 2014/0144429 A1 | 5/2014 | Wensley et al. | |
| 2014/0196736 A1 | 7/2014 | Fernando et al. | |
| 2014/0209109 A1 | 7/2014 | Larson | |
| 2014/0251355 A1 | 9/2014 | Tracey | |
| 2014/0283824 A1 | 9/2014 | Wheelock et al. | |
| 2014/0283855 A1 | 9/2014 | Hawes et al. | |
| 2014/0299141 A1 | 10/2014 | Flick | |
| 2014/0305448 A1 | 10/2014 | Zuber et al. | |
| 2014/0314397 A1 | 10/2014 | Alima | |
| 2014/0318559 A1 | 10/2014 | Thorens et al. | |
| 2014/0345633 A1 | 11/2014 | Talon et al. | |
| 2014/0348495 A1* | 11/2014 | Greim | H05B 3/02 392/386 |
| 2014/0360517 A1 | 12/2014 | Taggart et al. | |
| 2014/0366898 A1 | 12/2014 | Monsees et al. | |
| 2014/0366900 A1 | 12/2014 | Plojoux et al. | |
| 2014/0373857 A1 | 12/2014 | Steinberg | |
| 2015/0020825 A1 | 1/2015 | Galloway et al. | |
| 2015/0020832 A1 | 1/2015 | Greim et al. | |
| 2015/0027469 A1 | 1/2015 | Tucker et al. | |
| 2015/0040930 A1 | 2/2015 | Robinson et al. | |
| 2015/0101606 A1 | 4/2015 | White | |
| 2015/0150305 A1 | 6/2015 | Shenkal | |
| 2015/0163859 A1 | 6/2015 | Schneider et al. | |
| 2015/0217064 A1 | 8/2015 | Trzecieski | |
| 2015/0223520 A1 | 8/2015 | Phillips et al. | |
| 2015/0282525 A1 | 10/2015 | Plojoux et al. | |
| 2015/0351456 A1 | 12/2015 | Johnson et al. | |
| 2016/0051464 A1 | 2/2016 | Trzecieski | |
| 2016/0213066 A1 | 7/2016 | Zitzke et al. | |
| 2016/0331912 A1 | 11/2016 | Trzecieski | |
| 2017/0065776 A1 | 3/2017 | Trzecieski | |
| 2017/0095623 A1 | 4/2017 | Trzecieski | |
| 2017/0181471 A1 | 6/2017 | Phillips et al. | |
| 2017/0303597 A1 | 10/2017 | Tsui | |
| 2017/0360091 A1 | 12/2017 | Bless et al. | |
| 2018/0070647 A1 | 3/2018 | Monsees et al. | |
| 2018/0153209 A1 | 6/2018 | Balder et al. | |
| 2019/0297952 A1 | 10/2019 | Qiu | |
| 2019/0335819 A1 | 11/2019 | Watanabe | |
| 2020/0077710 A1 | 3/2020 | Volodarsky et al. | |
| 2020/0171266 A1 | 6/2020 | Trzecieski | |
| 2020/0288780 A1 | 9/2020 | Martin et al. | |

FOREIGN PATENT DOCUMENTS

| | | | |
|---|---|---|---|
| WO | WO2013098405 | * | 4/2013 |
| WO | 2013098411 A1 | | 7/2013 |
| WO | 2013098405 A3 | | 8/2013 |

OTHER PUBLICATIONS

Document relating to U.S. Appl. No. 14/829,660 dated Mar. 19, 2018 (Office Action).

Document relating to U.S. Appl. No. 14/614,005 dated Oct. 23, 2017 (Office Action).

Document relating to U.S. Appl. No. 16/269,638 , dated Oct. 6, 2020 (office Action), 24 page.

Document relating to co-pending U.S. Appl. No. 16/269,638, dated Jan. 22, 2021 (Notice of Allowance), 6 pages.

* cited by examiner

US 11,065,402 B2

AROMATHERAPY VAPORIZATION DEVICE

CROSS REFERENCE TO RELATED APPLICATIONS

This application is a continuation in part of U.S. patent application Ser. No. 14/614,005, filed on Feb. 4, 2015, which claims the benefit of U.S. Provisional Patent Application No. 61/935,349 filed on Feb. 4, 2014, and U.S. patent application Ser. No. 14/829,660 filed on Aug. 19, 2015, which claims the benefit of U.S. Provisional Patent Application No. 62/038, 863 filed on Aug. 19, 2014, and also claims priority from U.S. Provisional Patent Application No. 62/519,972, filed Jun. 15, 2017, the entire contents of each of which are hereby incorporated by reference.

FIELD OF THE INVENTION

This disclosure relates generally to vaporization devices, and in particular to vaporization devices that vaporize phyto material for aromatherapy.

BACKGROUND

The following is intended to introduce the reader to the detailed description that follows and not to define or limit the claimed subject matter.

Aromatherapy generally uses essential oils released from phyto materials, such as the leaves of plants, for therapeutic benefits. By heating phyto material to a temperature sufficient for vaporization, essential oils and extracts may be emitted from the phyto material as vapor. This vapor may be inhaled by a user for its therapeutic benefits. Different phyto materials release vapors at different temperatures. For example, some phyto materials release vapor at 120 degrees Celsius, while others release vapor at 220 degrees Celsius. Devices that can heat phyto material to a temperature sufficient to release the vapor are generally known as vaporizers. Various devices for vaporizing phyto materials for aromatherapy are known.

SUMMARY

The following introduction is provided to introduce the reader to the more detailed description to follow and not to limit or define any claimed or as yet unclaimed invention. One or more inventions may reside in any combination or sub-combination of the elements or process steps disclosed in any part of this document including its claims and figures.

In accordance with a first aspect of this disclosure, there is provided a vaporization device. The vaporization can include a housing extending from a first end to a second end; a heating chamber disposed at the first end of the housing, the heating chamber having a first chamber end proximate the first end of the housing, a second chamber end displaced from the first end towards the second end and a chamber wall extending between the first chamber end and the second chamber end, wherein a volume bounded by the first chamber end, the second chamber end and the chamber wall defines a phyto material receiving chamber, and wherein the first chamber end is open and the second chamber end is substantially closed and comprises one or more vents; an inhalation aperture formed proximate the second end of the housing; a heating element disposed within the heating chamber between the first chamber end and the second chamber end, the heating element configured to emit heat, wherein phyto material is receivable in the phyto material receiving chamber between the heating element and the chamber wall whereby heat emitted from the heating element is operable to at least partially vaporize the phyto material whereby a vapor is emitted; an energy storage member at least partially disposed within the housing; a control circuit electrically coupled to the energy storage member and to the heating element, the control circuit configured to control the flow of electrical current from the energy storage member to the heating element, the control circuit further comprising a user-activated switch for controlling the flow of electrical current from the energy storage member to the heating element; a first fluid pathway extending through the housing from the first end to the second end, the fluid pathway being fluidly coupled to the phyto material receiving chamber and to the inhalation aperture; an ambient air input port; and a second fluid pathway extending between the ambient air input port and a second fluid pathway end disposed proximate the second chamber end, the second fluid pathway end fluidly coupled to the inhalation aperture, the second fluid pathway comprising a puff sensor coupled to the control circuit, the puff sensor operable to detect the flow of ambient air through the second fluid pathway and to generate an airflow signal in response to detecting the flow of ambient air, wherein the control circuit is operable to control the flow of electrical current from the energy storage member to the heating element in response to the airflow signal; wherein, upon activation of the switch, electrical current from the energy storage member is enabled to be provided to the heating element; and upon creation of a low pressure at the inhalation aperture, a reduced pressure region is created in the first fluid pathway and ambient air is induced to flow into the heating chamber via the first end and propagate through the vapor emitted from heating the phyto material, whereby the vapor mixes with the ambient air and together flows through the fluid pathway to the inhalation aperture, and ambient air separately enters the ambient air input port whereby the puff sensor is triggered.

In some embodiments, the heating element can be a blade-shaped heating element.

In some embodiments, the blade-shaped heating element can include two parallel flat long sides and two parallel flat narrow sides and a majority of the heat from the heating element radiates from the two parallel flat long sides outwardly towards the chamber wall.

In some embodiments, the heating chamber can be cylindrical and the first chamber end can have a sharpened peripheral edge.

In some embodiments, the heating element can be a rod-shaped heating element.

In some embodiments, the first fluid pathway can include a thermally conductive material proximate the inhalation aperture to provide heat transfer between ambient air and the mixed vapor and air flowing through the fluid pathway.

In some embodiments, the closed end can include a sliding member that is movable between a first position in which the sliding member is proximate to the second chamber end and second position in which the sliding member is proximate to the first chamber end.

In some embodiments, the user-activated switch may be a mechanical switch.

In accordance with an aspect of the disclosure, there is provided a vaporization device. The vaporization device includes a housing extending axially between a first housing end and a second housing end; a fluid pathway extending through the housing between the first housing end and the second housing end; an inhalation aperture fluidly coupled to the fluid pathway, the inhalation aperture positioned at the second housing end; a heating element heatable to at least one predetermined vaporization temperature, wherein in use the predetermined vaporization temperature is selected to vaporize phyto material proximate the heating element whereby a phyto material vapor is emitted; an energy storage member disposed within the housing and electrically coupled to the heating element; and a control circuit disposed within the housing and electrically coupled to the energy storage member, the control circuit having a user-activated switch operable to control a flow of electric current from the energy storage member to the heating element, wherein, in response to a user inhalation at the inhalation aperture, a pressure gradient is created across the fluid pathway that draws ambient air from the external environment into the fluid pathway and the ambient air mixes with the phyto material vapor, and the mixed vapor and air are drawn through the fluid pathway to the inhalation aperture.

In some embodiments, the vaporization device may include a heating chamber proximate the first housing end, the heating chamber having a first heating chamber end, a second heating chamber end in fluid communication with the fluid pathway, and a chamber wall extending between the first heating chamber end and the second heating chamber end, the first heating chamber end, second heating chamber end and chamber wall together defining a heating chamber volume, wherein the first heating chamber end is open and the second heating chamber end is a substantially closed end comprising one or more vents.

In some embodiments, an inner portion of the fluid pathway can include a thermally conductive liner.

In some embodiments, the heating chamber can include a ceramic material.

In some embodiments, the user-activated switch may be a mechanical switch.

In some embodiments, the fluid pathway can include an airflow sensor electronically coupled to the control circuit, and the control circuit can be configured to determine a volume of ambient air entering the heating chamber based on airflow readings received from the airflow sensor and provide an indication that the phyto material in the internal cavity needs replacing when the determined volume of ambient air entering the heating chamber exceeds a predetermined volume threshold.

In some embodiments, the vaporization device can include a secondary fluid pathway extending between an ambient air input port and a secondary inhalation aperture, where the secondary inhalation aperture and the inhalation aperture are adjacent one another and are formed as a joint inhalation aperture at the second housing end, the secondary fluid pathway having a puff sensor therein configured to detect a flow rate within the secondary fluid pathway, where a primary pressure gradient is created across the fluid pathway and a secondary pressure gradient is created across the secondary fluid pathway in response to the user inhalation, the primary pressure gradient drawing a first volume of ambient air from the external environment into the heating chamber volume and the secondary pressure gradient drawing a second volume of ambient air from the external environmental into the air input port, and the second volume of ambient air triggers the puff sensor to detect the flow rate of the second volume of ambient air and send a puff signal to the control circuit to adjust the flow of the electric current from the energy storage member to the heating element based on the detected flow rate.

In some embodiments, a central axis of the housing can be offset from a central axis of the fluid pathway.

In some embodiments, the vaporization device can include a first contact and a second contact, the first contact and the second contact being electrically coupled to the control circuit and protruding from the housing, where the first contact and the second contact are respectively engageable with a first energy storage member recharging contact and a second energy storage member recharging contact of a recharging hub to provide electrical energy from the recharging port to the energy storage member.

In some embodiments, the vaporization device can include a heating chamber that defines a phyto material receiving area and the heating element can be positioned within the phyto material receiving area.

In some embodiments, the heating chamber may be cylindrical and the outer end of the heating chamber may have a pointed peripheral edge operable to cut phyto material when pressed against it.

In some embodiments, the heating element may include a blade aligned centrally within an internal cavity of the heating chamber, the blade can be configured to radiate heat outwardly.

In some embodiments, the heating element can be a rod-shaped heating element aligned centrally within an internal cavity of the heating chamber, the rod-shaped heating element can be configured to radiate heat outwardly In some embodiments, the heating element may contact a chamber wall of the heating chamber and can be configured to heat the chamber wall.

In some embodiments, the heating chamber extends between an outer heating chamber end and an inner heating chamber end in fluid communication with the fluid pathway, where the inner heating chamber end is a substantially closed end comprising one or more vents; the closed end includes a sliding member that is slideable between an open position and a closed position, in the opened position, the sliding member is spaced apart from the outer heating chamber end such that the phyto receiving area is accessible to receive phyto material; in the closed position, the sliding barrier is positioned proximate to the outer heating chamber end.

In some embodiments, the heating element includes a protruding portion that protrudes from the first housing end.

In some embodiments, the heating element may be a flat plate ceramic heating element.

In some embodiments, the device may include a cylindrical heating chamber that extends along a central axis; and the flat plate ceramic heating element may be offset from the central axis.

In some embodiments, the heating element may be a cylindrical heating element.

In accordance with an aspect of the disclosure, there is provided a vaporization device. The vaporization device can include a vaporization tube extending axially between an open first tube end and an open second tube end, the vaporization tube having an outer tube surface enclosing a fluid pathway extending between the first tube end and the second tube end, wherein the second tube end defining an inhalation aperture; a cylindrical heating element coupled to the outer tube surface proximate the open first tube end, the heating element being concentrically aligned with the vaporization tube, wherein the cylindrical heating element is operable to heat the fluid pathway at the open first tube end to a predetermined vaporization temperature, wherein in use the predetermined vaporization temperature is sufficient to vaporize phyto material in contact with the open first tube end; an energy storage member electrically coupled to the cylindrical heating element; and a control circuit electrically coupled to the energy storage member, the control circuit operable to control a flow of electric current from the energy storage member to the heating element, wherein, in response to a user inhalation at the inhalation aperture, a pressure gradient is created across the fluid pathway that draws ambient air from the external environment into the open tube first end and the ambient air mixes with the phyto material vapor, and the mixed vapor and air are drawn through the fluid pathway to the inhalation aperture.

In some embodiments, the vaporization tube can be a glass tube.

In some embodiments, the vaporization tube can include one of a fused quartz glass and a borosilicate glass tube.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which.

Figure 1:
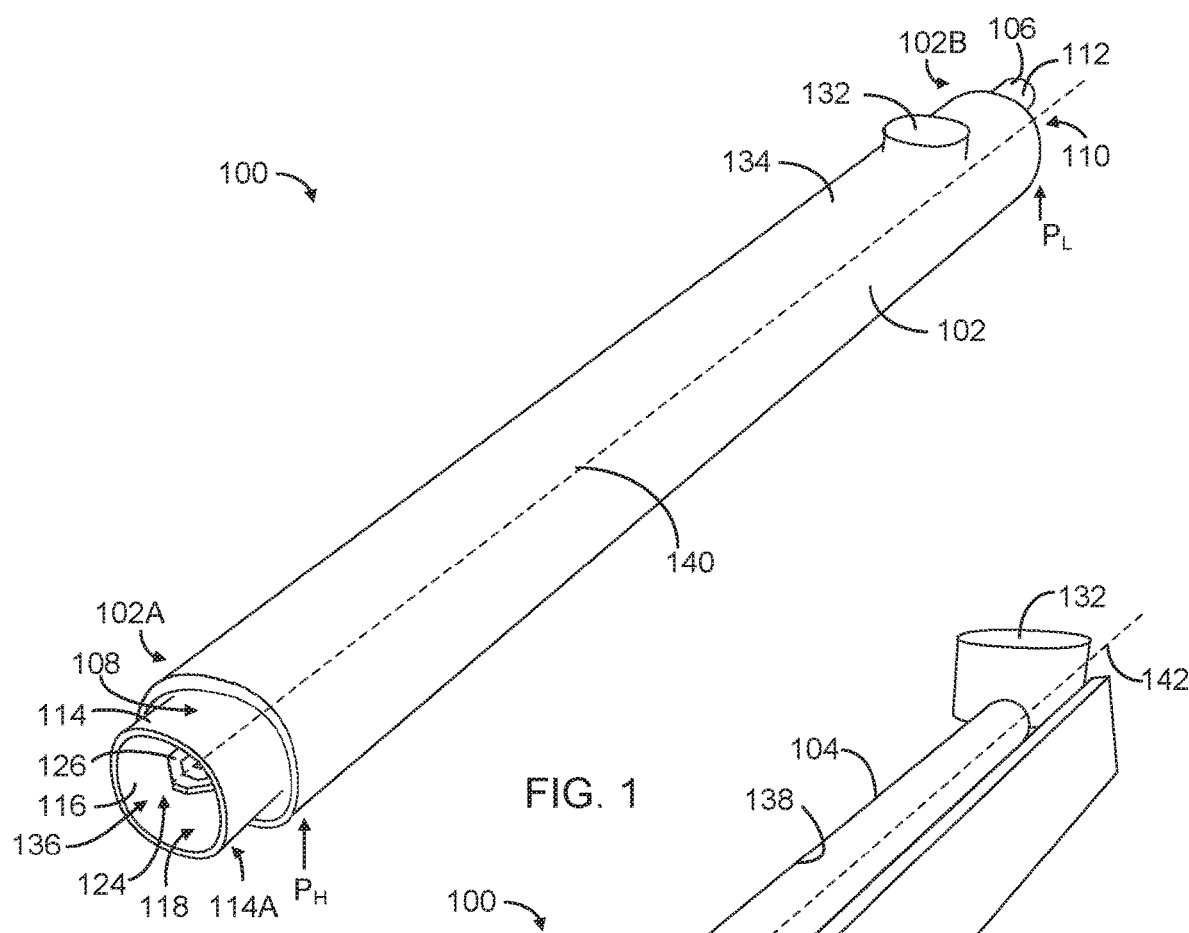
FIG. 1 is a top, front perspective view of an example vaporization device, in accordance with an embodiment.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising," and variations thereof mean "including but not limited to," unless expressly specified otherwise. A listing of items does not imply that any or all of the items are mutually exclusive, unless expressly specified otherwise. The terms "a," "an," and "the" mean "one or more," unless expressly specified otherwise.

Vaporization of phyto materials may emit vapors that can provide therapeutic benefits when inhaled by users. Devices used to heat phyto material to suitable vaporization temperatures are often referred to as vaporizers or vaporization devices.

Vaporization devices may include a heating chamber in which phyto material is heated and vaporized. The vaporization of the phyto material allows desired essential oils and other flavored extracts to be separated from the phyto material in vapor form and inhaled by a user of the device.

The heating time required by a vaporization device can impact the usability of the device. Devices with long heating times may result in delays between the time the device is activated and the vapor is emitted. This can negatively impact the user experience and may also result in additional drain on the device power source. For instance, the delay may result in a user leaving the device active for longer than necessary to ensure that the vaporization temperature has been reached, resulting in additional energy waste. Additionally, if phyto material is heated for a prolonged period of time, the potency of the desired essential oils and flavored extracts released as vapor may be reduced.

Controlling the heating of phyto materials placed in vaporization devices is also important for user experience and health. If phyto material is heated to its combustion temperature, the phyto material may combust and emit smoke rather than vapor. Careful control of the heat generated within the heating chamber may be required to ensure that the phyto material is vaporized rather than combusted.

Battery life may also impact usability of vaporization devices, particularly portable devices. Users may wish to use a portable vaporization device over the course of an extended period such as a day or multiple days. Individuals who use vaporization devices outdoors, or otherwise away from external power sources, may require a source of energy for an extended period of time. Vaporization devices with short battery life may not be suitable to such users. More generally, such vaporization devices may require more frequent charging or replacement of batteries, leading to more frequent periods when the device is not usable. This may further delay a user's ability to achieve the desired therapeutic effects.

Flexibility in recharging vaporization devices may be important, particular where the device is portable. Vaporization devices that use proprietary recharging connections may effectively prevent users from recharging the energy storage members while on the go, as there may not be suitable recharging stations accessible.

Embodiments described herein relate generally to vaporization devices. In general, the vaporization devices described herein may be used to vaporize phyto material derived from plant matter. In some cases, the vaporization devices described herein may also be used to vaporize materials extracted from phyto material, such a phyto material extracts and oils.

Various types of phyto material derived from plant matter may be vaporized for aromatherapy or medicinal treatment regimens. For instance, phyto material from cannabis plants, such as the buds and/or leaves, may be vaporized. A user may inhale the cannabis vapor generated from a vaporization device to achieve associated therapeutic effects.

Figure 2:
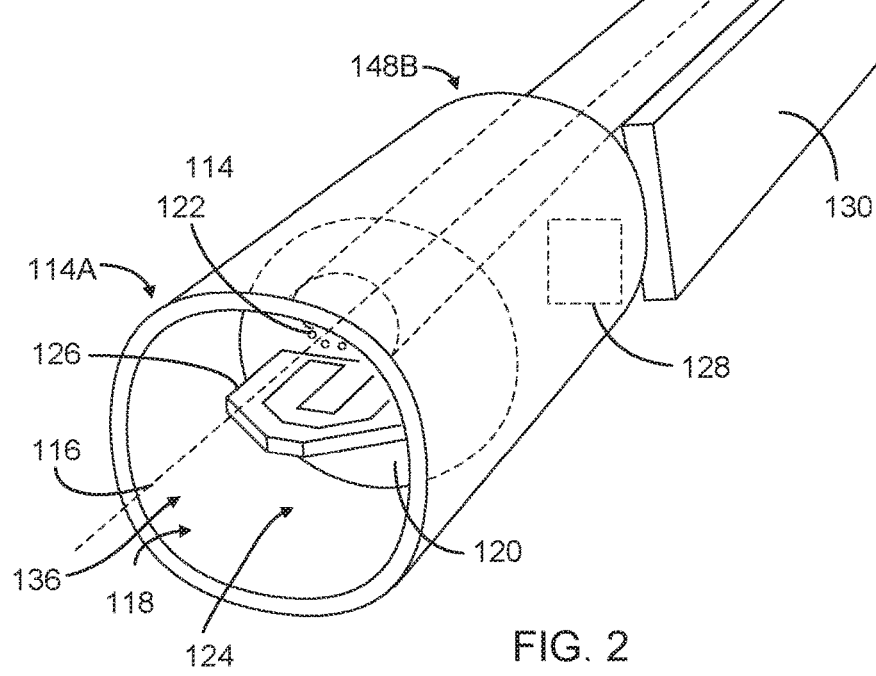
FIG. 2 is a top, front perspective view of the example vaporization device of FIG. 1 with a housing removed.

Referring generally to FIGS. 1-5, shown therein is an example of a vaporization device 100. FIG. 1 shows a perspective view of the vaporization device 100 including a housing 102. FIG. 2 illustrates the vaporization device 100 with the housing 102 removed to more clearly identify components positioned within the housing 102.

The housing 102 extends between a housing first end 102A and a housing second end 102B. The housing 102 may define a central axis 140 of the vaporization device 100.

In the example shown, the housing 102 defines a substantially cylindrically shaped vaporization device 100. This may provide a sleek profile for the vaporization device 100 that can improve portability and facilitate storage in a pocket. The circular cross-section of the vaporization device 100 may also provide a relatively strong exterior housing 102.

In some embodiments, the vaporization device 100 may include flattened or partially flattened sides. For instance, the housing 102 may be generally cylindrical in shape, with four or more partially flattened sides. Providing flattened, or partially flattened, sides may reduce the likelihood of the vaporization device 100 rolling off the edge of a table or other surface.

Alternatively, the vaporization device 100 may be rectangular or another suitable shape.

The housing 102 can enclose a fluid pathway 104 that extends between the housing first end 102A and the housing second end 102B. An inhalation aperture 106 is positioned at the housing second end 102B. The inhalation aperture 106 is fluidly coupled with the fluid pathway 104.

The first end 102A of the housing 102 may be an open housing end 108. Thus, the first end 102A may be exposed to an external environment.

In some cases, the second end 102B of the housing 102 may be a partially closed housing end 110. As shown, the second end 102B may be closed except for the inhalation aperture 106.

In the example shown, the inhalation aperture 106 extends from the closed housing end 110 to define a mouthpiece 112. Alternatively, the inhalation aperture 106 may be flush with the end 102B of the housing, e.g. an opening formed in the closed end 110 (see e.g. inhalation aperture 206 of FIG. 6).

Vaporization device 100 also includes a heating chamber 114 proximate to the housing first end 102A. The heating chamber 114 is in fluid communication with the fluid pathway 104. The heating chamber 114 can provide a phyto material receiving area in which phyto material can be positioned for vaporization.

As shown, the heating chamber 114 has a heating chamber first end 114A and a heating chamber second end 114B. A heating chamber wall 116 extends between the heating chamber first end 114A and the heating chamber second end 114B.

The first end 114A of the heating chamber 114 (also referred to as the outer end) may be an open chamber end 118. The open chamber end 118 can expose the heating chamber 114 and allow access to the phyto material receiving area. Having the first end 114A open also allows ambient air to be drawn into the heating chamber 114.

Optionally, the heating chamber 114 may include a closure member or lid. The closure member may be detachably attachable to the first end 114A of the heating chamber 114. This may allow the heating chamber 114 to be substantially closed when phyto material is positioned in the heating chamber 114 to be vaporized. The closure member may include one or more ambient air inlets to allow ambient air to be drawn into the heating chamber 114 when the closure member is positioned on the first end 114A.

The second end 114B of the heating chamber 114 (also referred to as the inner end) may be a substantially closed chamber end 120. The second end 114B of the heating chamber 114B may be closed (i.e. fluidly sealed) with the exception of one or more vents, or vapor inlets 122. Each vapor inlet 122 can extend through the closed chamber end 120. The vapor inlets 122 can fluidly couple the heating chamber 114 to the fluid pathway 104.

In some embodiments, the heating chamber 114 may be housed entirely within housing 102. For instance, the heating chamber first end 114A may not extend out from the housing first end 102A (see e.g., FIG. 6). The housing 102 may enclose the wall 116 of the heating chamber 114. In some embodiments, the inner surface of the housing 102 may provide the wall 116 of the heating chamber 114.

Alternatively, the housing 102 may provide an external insulation layer exterior to the wall 116. This may reduce the likelihood of a user burning themselves as a result of the heating chamber 114 being hot when vaporizing phyto material.

Alternatively, the heating chamber 114 may protrude at least partially from the first end 102A of the housing 102 as shown. This may promote only the heating chamber 114, and components therein, coming into direct contact with the phyto material.

The heating chamber 114 can also define a phyto material receiving area. The phyto material receiving area of vaporization device 100 may be defined as a volume bounded by the chamber wall 116, the heating chamber first end 114A and the heating chamber second end 114B. As shown, the phyto material receiving area may be an internal heating chamber cavity into which phyto material can be positioned. Phyto material to be vaporized may be loaded into the internal cavity 124 through the open chamber end 118.

Vaporization device 100 also includes a heating element 126. The heating element 126 is operable to heat phyto material to a predetermined vaporization temperature. The predetermined vaporization temperature may vary depending on the type of phyto material being vaporized. For instance, the vaporization temperatures for various cannabis phyto materials and extracts that may typically be vaporized can range between about 300 degrees Fahrenheit to about 450 degrees Fahrenheit.

In some embodiments, the heating element 126 may be heatable to temperatures that range from about 330 degrees Fahrenheit to about 900 degrees Fahrenheit. This may also allow the heating element 126 to perform a cleaning function in which excess or spent phyto material can be incinerated.

The heating element 126 can be configured to generate heat at the predetermined vaporization temperature. As shown in FIG. 2, the conductive heating element 126 can extend into the heating chamber 114. The heating element 126 may extend from the second chamber end 114B into the internal cavity 124 of the heating chamber 114. The heating element 126 may operate to vaporize phyto material positioned within the heating chamber 114.

The heating element 126 may be positioned centrally within the heating chamber 114. As shown in FIG. 2, the heating element 114 may extend along a plane that includes the central axis 140 of the vaporization device 100. The conductive heating element 126 may be configured to outwardly radiate heat within the internal cavity 124 toward the chamber wall 116. This may allow the heating element 126 to more evenly heat the heating chamber 114.

In the illustrated example, phyto material may be loaded into the phyto material receiving chamber 114 between the heating element 126 and the chamber wall 116. Outwardly radiating heat at the predetermined vaporization temperature, generated from the heating element 126, may at least partially vaporize the phyto material. Phyto material vapor may then be emitted and drawn into the fluid pathway 104.

The heating element 126 may be a conductive heating element that is heatable using electrical current. The heating element 126 can be electrically connected to a power source, such as an onboard energy storage member. Current from the power source can be discharged through the heating element 126 which can dissipate the energy into the heating chamber 114 as heat. The heating element 126 may radiate heat into the heating chamber 114, and into any phyto material in contact therewith (or in proximity thereto).

Vaporization device 100 can also include an energy storage member 128. The energy storage member 128 may be one or more batteries or a battery pack. The energy storage member 128 can be electrically coupled to the conductive heating element 126.

Vaporization device 100 can also include a control circuit 130 electrically coupled to the energy storage member 128. Control circuit 130 may be configured to control the flow of electrical current from the energy storage member 128 to the conductive heating element 126. The control circuit 130 may be implemented using various control components, such as a microprocessor, FPGA and/or application specific circuitry.

As shown in FIGS. 1 and 2, the energy storage member 128 and control circuit 130 can be disposed within the housing 102. The housing 102 may fully enclose the energy storage member 128 and the control circuit 130. The housing 102 may prevent dirt or debris from clogging the energy storage member 128 and the control circuit 130, which may be particularly useful when the vaporization device 100 is used outdoors. The housing 102 may also provide some protection from damage due to impacts.

Alternatively, the battery 128 and/or control circuit 130 may be at least partially exposed by the housing 102. This may provide easier access to the battery 128 or control circuit 130 for repair or replacement.

In the illustrated example, the vaporization device 100 includes a switch 132. The switch 132 may be user-activated to control the flow of current from the battery 128 to the conductive heating element 126. For instance, the switch 132 may be implemented using a mechanical switch, a hall-effect switch, or even a touchscreen display. In some cases, the switch 132 may be activated in response to detecting air flow through the vaporization device 100, e.g. as a result of a user inhaling from the inhalation aperture 106.

As shown in FIG. 1, the user activated-switch 132 can protrude from the housing 102. Alternatively, however, the switch 132 may be flush with the surface of housing 102, or even recessed therein.

As shown in FIG. 1, the switch 132 can be positioned proximate the housing second end 102B. This may allow a user to hold the vaporization device 100 near the inhalation aperture 106 and operate the switch 132 using the same hand.

Figure 6:
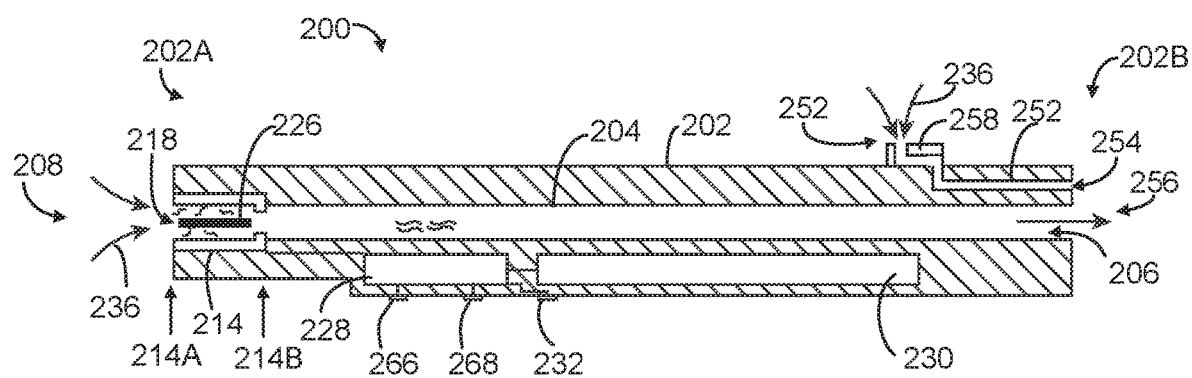
FIG. 6 is a cut-away side view of another example vaporization device, in accordance with an embodiment.

Alternatively, user-activated switch 132 may also be positioned elsewhere alone the length of the vaporization device (see e.g., user-activated switch 232 of FIG. 6).

Optionally, the vaporization device 100 may include additional control and configuration inputs and/or outputs. For instance, the vaporization device 100 may include a temperature output indicating the predetermined vaporization temperature. In some embodiments, the predetermined vaporization temperature may be adjustable using a temperature setting input, such as a touchscreen, switch or dial.

The switch 132 may be moveable between an active position and an inactive position. When the switch is in the active position, the flow of current from the battery 128 to the conductive heating element 126 can be enabled. When the switch is in the inactive position, current can be prevented from flowing from the battery 128 to the conductive heating element 126.

The switch 132 can be connected to control circuit 130. The control circuit 130 may control the flow of current from the battery 128 to the heating element 126 to ensure that the heating element 126 is heated to the predetermined vaporization temperature.

In some embodiments, the switch 132 may activate the control circuit 130 when moved to the active position. When the control circuit 130 is active, the control circuit 130 may permit current to flow to the heating element 126.

In some embodiments, activating the switch 132 may cause the control circuit 130 to direct current from the battery 128 to the heating element 126. Alternatively, the control circuit 130 may selectively provide currently to the heating element 126, e.g. in response to sensor readings from an airflow or puff sensor as described herein below.

In the illustrated example, when current is provided to the heating element 126, the conductive heating element 126 can heat phyto material received within the heating chamber 114. When the phyto material is heated to the predetermined vaporization temperature, a phyto material vapor is emitted.

In operation, a user may inhale from the inhalation aperture 106. In response to a user inhaling from the inhalation aperture 106, a pressure gradient can be created across the fluid pathway 104. As shown is FIG. 1, a reduced pressure region $P_L$ can result at the housing second end 102B. This reduced pressure region $P_L$ is a region of lower pressure as compared to the pressure $P_H$ at the housing first end 102A.

A user inhaling from inhalation aperture 106 can draw ambient air 136 from the external environment into the heating chamber 114 through open chamber end 118. As it flows through the heating chamber 114, the ambient air 136 can mix with vapor emitted from the phyto material being vaporized. The mixed vapor and air is drawn by the pressure gradient through the fluid pathway 104 to the inhalation aperture 106. The mixed vapor and air then exits the vaporization device 100 and can be inhaled by the user through inhalation aperture 102.

Optionally, the vaporization device 100 may include a thermally conductive section coupled to the fluid pathway 104. The thermally conductive section may be proximate the inhalation aperture 104, near the housing second end 102B. The thermally conductive section may provide heat transfer between ambient air external to the vaporization device 100 and the mixed vapor and air flowing through the fluid pathway 104. This may cool the mixed vapor and air as it approaches the inhalation aperture 106, so that the mixture inhaled by a user is not so hot that it scalds or injures them.

Optionally, an inner portion 138 of the fluid pathway 110 may include a thermally conductive liner. This conductive liner may also serve to reduce the temperature of the vapor and air flowing through fluid pathway 104.

The thermally conductive portion may include a section of material that provides greater thermal conductivity from the rest of housing 102. For instance, housing 102 may be formed generally using glass materials, while the thermally conductive portion may include metallic materials.

In some embodiments, the vaporization device 100 may include one or more sensors operable to monitor the flow of air through the fluid pathway 104. For example, an airflow sensor (not shown) may be positioned within the fluid pathway 104. The airflow sensor may operate to detect air flow through the fluid pathway 104. In some embodiments, the airflow sensor may also detect an airflow rate (i.e. the volume of air/vapor being drawn through the fluid pathway per unit time) through the fluid pathway 104.

The airflow sensor can be electronically coupled to the control circuit 130. The airflow sensor can transmit airflow signals to the control circuit 130. In some embodiments, the airflow signals from the airflow sensor may be used to trigger the supply of current to the heating element 114.

The control circuit 130 can be configured to monitor the airflow through the fluid pathway 104 in response to the airflow signals from the airflow sensor. For example, the control circuit 130 may detect airflow through the heating chamber 114 using the signals from the airflow sensor. In some cases, the control circuit 130 may determine the volume of ambient air 136 being drawn through the heating chamber 114.

In some embodiments, the control circuit 130 may initiate heating of the heating element 126 in response to signals from the airflow sensor. For example, the control circuit 130 may provide current to the heating element immediately in response to detecting airflow through the fluid pathway 104. This may ensure that the phyto material can be vaporized when a user is inhaling from the vaporization device 100, without over-heating the phyto material or having a prolonged heating period. In some embodiments, the control circuit 130 may also cease the provision of current to the heating element 114 when airflow is no longer detected or if the airflow rate drops below a threshold value.

In some embodiments, the heating element 126 of vaporization device 100 may be heated in response to signals from the airflow detector. For instance, the switch 132 may operate as an on/off switch activating the control circuit 130, and the control circuit 130 may provide current to heating element 126 in response to the detection of a user inhaling from the vaporization device 100.

The time required for the heating element 126 to be heated to a predetermined vaporization temperature may vary depending on the specific configuration of the heating element 126. Accordingly, it may be preferable for the heating element 126 to be activated in response to airflow signals only in embodiments in which the heating element 126 can be heated sufficiently rapidly to vaporize phyto material while the user continues to draw in air from inhalation aperture 106.

For example, the inventor has found that ceramic plate heating elements (such as those shown in FIGS. 1-5, 13 and 14) with a heating element resistance of 0.5 Ohm and a voltage of 7V applied across the heating element can be heated to about 500 F to 700 F in about 8 to 10 seconds. The inventor has also found that a rod (spike) heating element (such as those shown in FIGS. 7, 8, and 9) with 0.2 Ohm heating element resistance and a voltage of 7V applied across the heating element can be heated to about 500 F to 700 F in about 3 to 5 seconds. Using a coil heating element (such as those shown in FIGS. 16-17) with a resistance of about 0.1-0.2 Ohms and applying a voltage of 3.7V across the heating element, the inventor has found that the heating element can be heated to about 500 F to 700 F in about 3 to 5 seconds. Accordingly, it may be preferable to use coil-based heating elements or rod heating elements when the heating elements are heated in response to a user inhaling.

In some embodiments, the control circuit 130 may also use the airflow sensor signals to monitor the state of the phyto material positioned in the heating chamber 114. For example, the heating chamber 114 may be sized to accommodate a defined volume of phyto material. By monitoring the volume of ambient air drawn through the heating chamber 114 and the predetermined vaporization temperature of the heating element 126, the control circuit 130 may determine that phyto material positioned within the heating chamber 114 has been substantially vaporized. The control circuit 130 may then provide an indication to the user (e.g. a visible or audible signal) that the phyto material in the heating chamber 114 may need to be replaced.

In some embodiments, the control circuit 130 may be configured to monitor a dose of phyto material consumed by a user of the vaporization device 100. The control circuit 130 may estimate a dose consumed by a user based on the size of the phyto material receiving area and the airflow through the heating chamber 114 when the phyto material is heated to a vaporization temperature. In some cases, a predefined quantity of phyto material may be inserted into the internal cavity 124 of the heating chamber 114, and the control circuit 130 may monitor the airflow through the heating chamber 114 to estimate the dose consumed by a user.

In some embodiments, the vaporization device 100 may include a temperature sensor (not shown). The temperature sensor may be positioned proximate to, or within, the heating chamber 114 to measure a temperature of the internal cavity 124.

The temperature sensor may be electronically coupled to control circuit 130. The temperature sensor may be configured to transmit temperature readings to the control circuit 130. The control circuit 130 may adjust the flow of electric current from the battery 128 to the conductive heating element 126 based on the received temperature readings to retain the heating chamber 114 at the predetermined vaporization temperature.

In some embodiments, the control circuit 130 may provide an indication to the user (e.g., a visible or audible output) that the predetermined vaporization temperature has been reached. This may alert the user that vapor is being emitted and can be inhaled.

In the example shown in FIG. 1, the housing 102 extends axially along a central axis 140. The fluid pathway 104 extends axially along a fluid pathway central axis 142 that extends generally between the housing first end 102A and the housing second end 102B. In the illustrated example, the central axis 142 of the fluid pathway 104 is offset from the central axis 140 of the housing 102. Offsetting the fluid pathway 104 within the housing 102 can allow the battery 128 and control circuit 130 to occupy more than 50% of the space within the housing 102. This may provide a more compact vaporization device 100, as the fluid pathway 104 may occupy less than 20% of the vertical space within the housing 102 for the majority of the longitudinal length of the housing 102.

Figure 9:
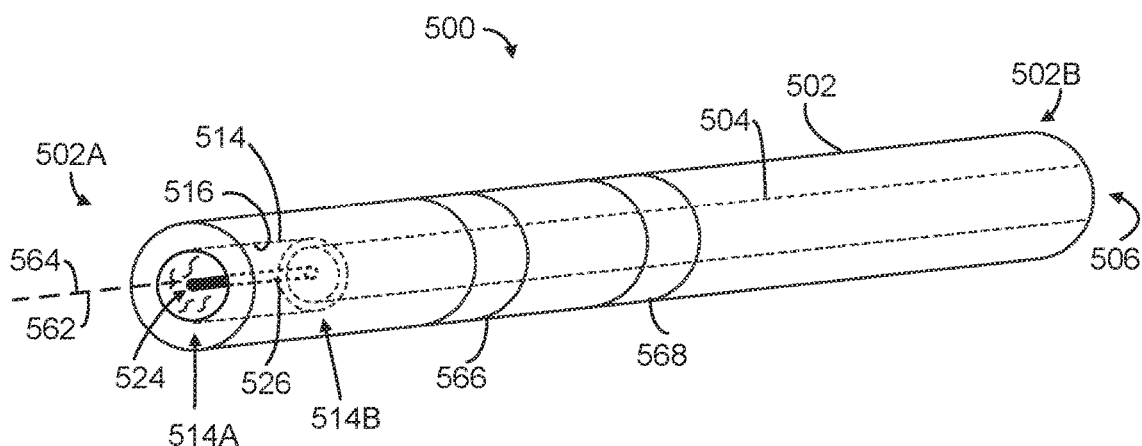
FIG. 9 is a perspective view of the example vaporization device of FIG. 8.

Alternatively, the housing central axis 140 and the fluid pathway central axis 142 may be co-axial (see e.g. FIG. 9).

Figure 3:
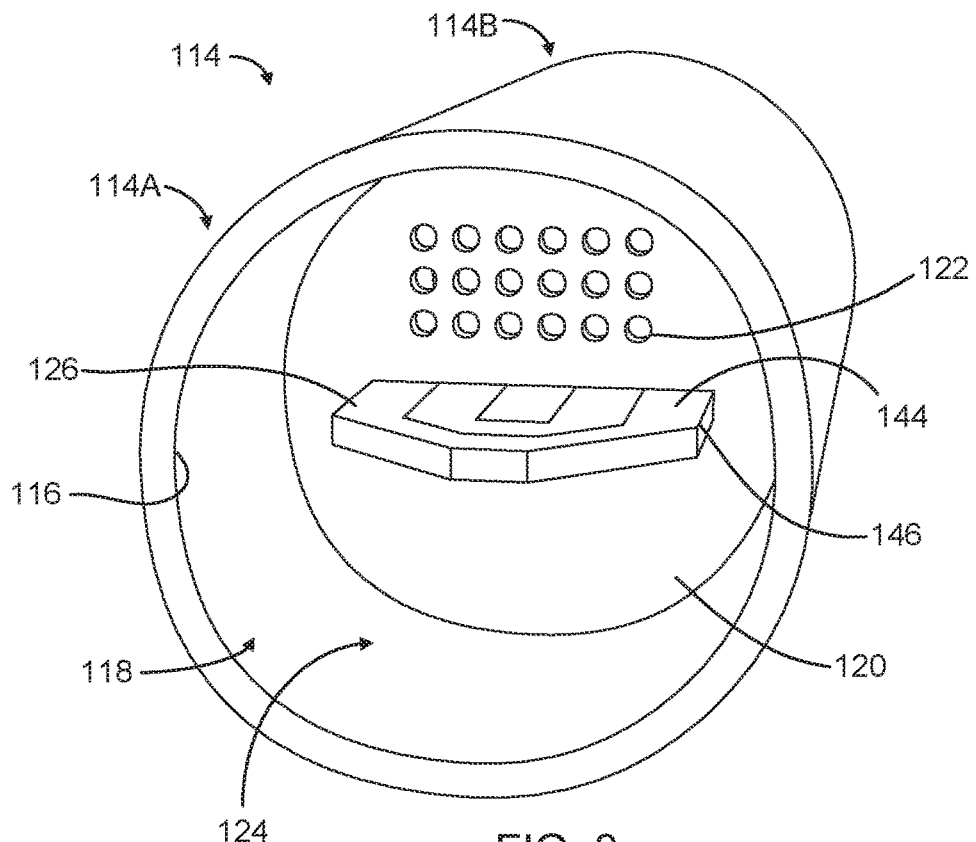
FIG. 3 is a front perspective view of a heating chamber of the example vaporization device of FIG. 1 with a moveable member in a first position.

As shown in FIG. 3, the heating element 126 may extend into the internal cavity of the heating chamber 114. The heating element 126 may be positioned centrally within the heating chamber 114. This may allow the heating element 126 to contact phyto material positioned through the heating chamber 114. By positioning the heating element 126 in direct contact with phyto material, the phyto material may be heated more efficiently.

In some embodiments, the heating element 126 may also be thermally coupled to the chamber wall 116. For example, the second end 114B of the housing 114 may be formed of a thermally conductive material. The second end 114B may transfer heat from the heating element 126 to the chamber wall 116. The chamber wall 116 may, in turn, heat phyto material positioned within the heating chamber 114.

As shown in FIG. 3, the conductive heating element 126 may be a blade-shaped heating element. In the illustrated example, the blade-shaped heating element can be aligned centrally within the internal cavity 124 of the heating chamber 114. Heat generated by the blade-shaped heating element can radiate outwardly toward the chamber wall 116.

The heating element 126 may be manufactured of various materials. For instance, the heating element may be manufactured of ceramic materials, such as alumina ceramic.

In some cases, the heating element 126 may be manufactured using high-temperature co-fired ceramics. For example, the heating element 126 may comprise a combination of high melting point metal heating materials such as tungsten, molybdenum, and/or molybdenum-manganese along with alumina ceramic substrates. The heating element 126 may be formed using a metal heating resistance slurry that is printed onto a ceramic green body in the desired configuration. This combination may be fired at a temperature of about 1500~1600 degrees Celsius along with a sintering additive, to form an alumina ceramic heating element.

In the illustrated example, the heating chamber 114 may be manufactured using ceramic materials. In some embodiments, chamber wall 116 is a ceramic material while the closed chamber end 120 may be metallic. Manufacturing the closed chamber end 120 using metallic materials may facilitate formation of the one or vents 122. In some embodiments, the heating chamber 114 may be formed with a ceramic exterior layer and the housing element 126 formed there within.

The housing 102 may be manufactured using various material, such as metallic materials. For instance, the housing 102 may be manufactured of gold plated copper, anodized aluminum or a TiN plated metal. In some cases, the housing 102 may be thermally conductive. This may allow the housing 102 to provide heat transfer between the fluid pathway 104 and the external environment.

In the example illustrated in FIG. 3, the blade-shaped heating element is a substantially planar heating element. The blade-shaped heating element 126 includes two parallel flat long sides 144 and two parallel flat narrow sides 146. In this configuration, a large portion of the heat radiates from the two parallel flat long sides 144 and outwardly toward the chamber wall 140. By providing the heating element 126 with an extended surface area along the long sides 144, the surface area in contact with the phyto material can be increased while still providing a large phyto material receiving space.

Alternatively, the heating element may be a circular or other shaped heating element extending into the heating chamber 114. For instance, the heating element may be shaped as a cylindrical rod or spike (see e.g. FIGS. 6, 8, and 9).

Figure 10:
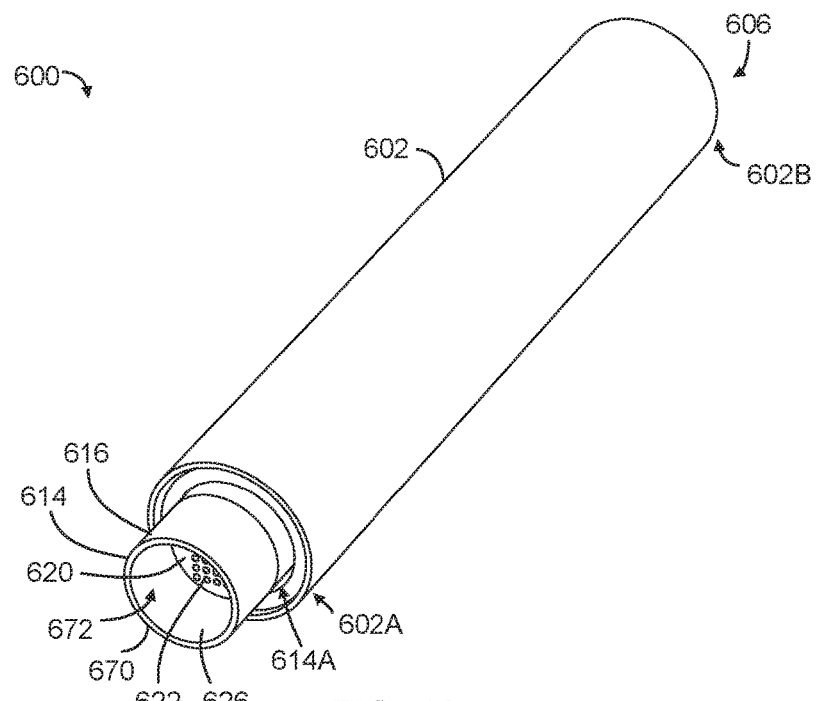
FIG. 10 is a perspective view of another example vaporization device, in accordance with an embodiment.

Alternatively, the heating element may be positioned to contact the chamber wall 116 of the heating chamber 114 (see e.g. FIG. 7) or integrated with the chamber wall 116 (see e.g. FIG. 10). For instance a cylindrical heating element may be formed on the inner surface of the chamber wall 116, or embedded into the chamber wall 116. Alternatively, the heating element may be positioned to contact an outer surface of the chamber wall 116, and the chamber wall 116 may transfer the heat from the heating element to the phyto material positioned within the heating chamber 114.

Figure 4:
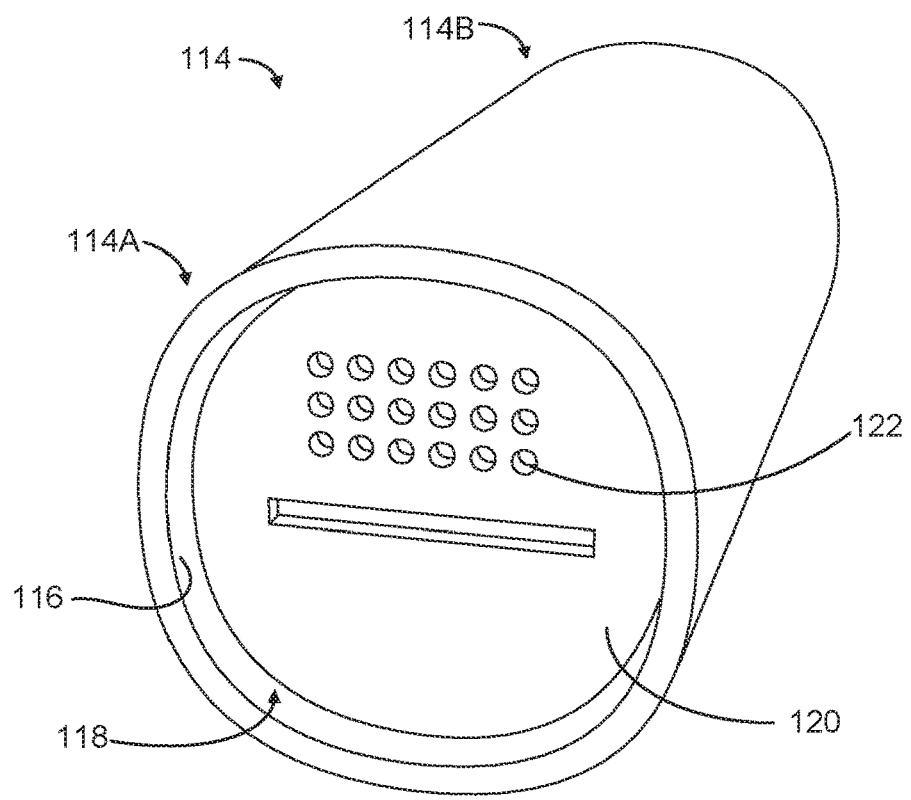
FIG. 4 is a front perspective view of the heating chamber of FIG. 3 with the moveable member in a second position.

In some embodiments, the heating chamber 114 may include a sliding member. In the example shown by FGIS. 3-4, the sliding member may defined the closed end 120 of the heating chamber 114. The sliding member may be moveable between a first position (also referred to as a load position), an example of which is shown in FIG. 3, and a second position (also referred to as an eject position), an example of which is shown in FIG. 4.

In the first position, the sliding member 120 can be positioned proximate to the heating chamber second end 114B. This may provide a user with access to the phyto material receiving area, e.g. to allow phyto material to be loaded and/or to facilitate cleaning.

In the second position, the sliding member 120 can be positioned proximate to the heating chamber first end 114A. The sliding member 120 may transition from the first position to the second position to eject phyto material from the phyto material receiving area. The second position may also facilitate cleaning the closed end 120 of the heating chamber 114, e.g. by providing easy access to vapor inlets 122.

Figure 5:
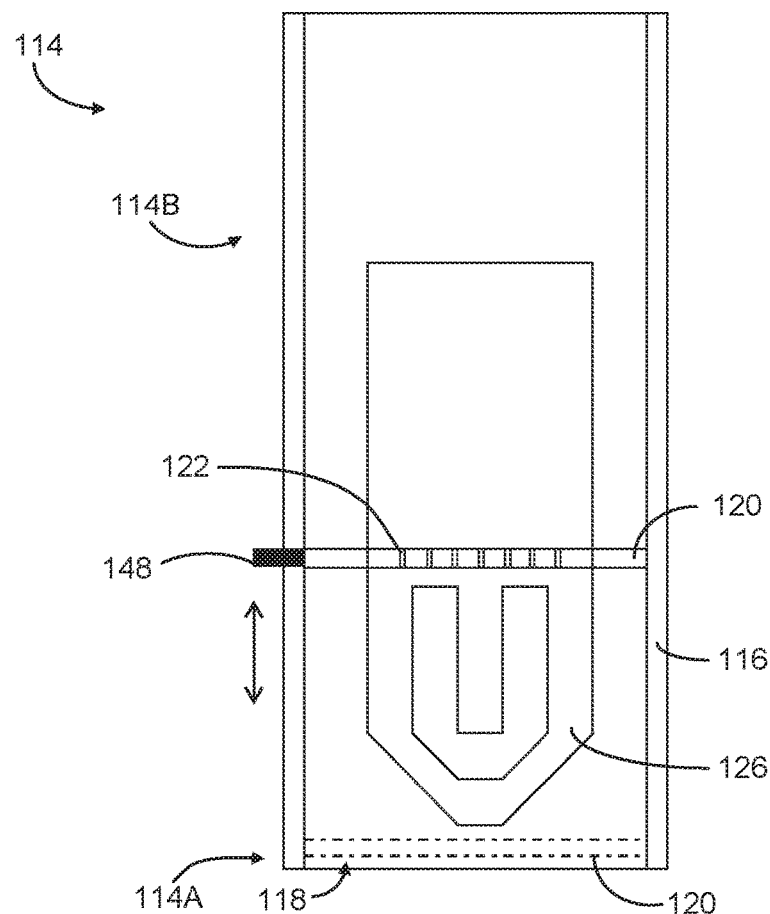
FIG. 5 is a cut-away top plan view of the heating chamber of FIG. 3.

As shown in the example of FIG. 5, the sliding member 120 may be manually adjustable between the first position and the second position. An actuator 148 may be provided on the vaporization device 100 to allow a user to move the sliding member between the first and second positions. For instance, the actuator 148 may be a switch or paddle.

In some embodiments, the sliding member 120 may be biased to the first position. For instance, the actuator 128 may include a spring-loaded trigger. A user may adjust the sliding member 120 to the second position when ejecting phyto material. The sliding member 120 may then automatically retract to the first position in the absence of user intervention.

In some embodiments, the sliding member 120 may provide a cover for the heating element 126. As shown in FIGS. 3 and 4, the sliding member 120 may also include a void or slot corresponding to the heating element 126. Thus, the heating element 126 may remain stationary when the sliding member 120 is moved between the first and second positions. This may facilitate construction, as the sliding member 120 may not include any active components.

The sliding member 120 may also protect the heating element 126 when the vaporization device 100 is not in use. For instance, the sliding member 120 may be adjustable to the closed/eject position when the device is not being used so that the heating element 126 is recessed behind sliding member 120.

As described above, the closed chamber end 120 includes one of more vents or vapor inlets 122. In the illustrated example, the heating chamber 114 includes eighteen vents 122. However, various other numbers and arrangements of vapor inlets may be provided in the heating chamber 114.

The vents 122 can be sized to inhibit phyto material from being drawn into the fluid pathway 104. In some cases, a screen or filter may be provided to prevent phyto material from entering the fluid pathway 104.

In some embodiments, the vapor inlets 122 may be provided only on a first side of the heating element 126 as shown in FIGS. 3 and 4. This may allow the fluid pathway 104 to be offset from the central axis 140 of the vaporization device 100 throughout the length of vaporization device 100.

Alternatively, vapor inlets 122 may be distributed around the heating element 122. This may facilitate drawing vapor and ambient air into the fluid pathway 104.

In some embodiments, the vaporization device 100 may also include a cleaning setting. The cleaning setting may facilitate discarding phyto material from the heating chamber 114. When the cleaning setting is activated (e.g. by a user activating a cleaning input setting), the control circuit 130 may operate to heat the heating element 126 to a combustion temperature of the phyto material (e.g. a temperature of 900 Fahrenheit or greater). The heating element may then incinerate phyto material debris positioned in the heating chamber that may otherwise be stuck on the inner surfaces of the heating chamber 114 or heating element 126. The incinerated phyto material may then be removed from the vaporization device 100, e.g. manually or using a sliding member 120.

FIG. 6 illustrates another example vaporization device 200 in accordance with an embodiment. Elements having similar structure and/or performing similar function as those in the example vaporization device 100 in FIGS. 1 to 2 are numbered similarly, with the reference numerals incremented by 100.

As shown in the example of FIG. 6, a housing 202 encloses a primary fluid pathway 204. The primary fluid pathway 204 extends axially between a housing first end 202A and a housing second end 202B. A primary inhalation aperture 206 is formed through the housing 202 at the housing second end 202B. The primary inhalation aperture 206 is in fluid communication with the primary fluid pathway 204.

Vaporization device 200 also includes a secondary air input port 250 coupled to a secondary fluid pathway 252. The secondary fluid pathway 252 extends between the secondary air input port 250 and the housing second end 202B.

In the example shown, vaporization device 200 includes a secondary inhalation aperture 254 positioned proximate the housing second end 202B. The secondary inhalation aperture 254 can be positioned adjacent to the inhalation aperture 206. A user inhaling from the device 200 may then draw air through both the primary inhalation aperture 206 and secondary inhalation aperture 254.

The secondary inhalation aperture 254 and primary inhalation aperture 206 may be joined in a common mouthpiece at the housing second end 202B. This may ensure that a user draws air through both the primary inhalation aperture 206 and secondary inhalation aperture 254.

In some embodiments, the secondary fluid pathway 252 may join the primary fluid pathway 204 upstream from the inhalation aperture 206. This may allow the device 200 to include only a single inhalation aperture.

As shown in FIG. 6, the primary fluid pathway 204 can be positioned centrally within the housing 202. This may facilitate providing a secondary fluid pathway 252 within housing 202.

Alternatively, the primary fluid pathway 204 may be offset from the central axis of housing 202 (as described above). In some such embodiments, the secondary fluid pathway 252 may join the primary fluid pathway 204 proximate the inhalation aperture 206 so that the secondary fluid pathway 252 may also be entirely contained within housing 202.

In some cases, offsetting the primary fluid pathway 204 may allow the secondary fluid pathway 252 to be formed on the opposite side of the vaporization device 200.

The vaporization device 200 may include a puff sensor 258 positioned in the secondary fluid pathway 252. The puff sensor 258 may operate to detect airflow through the secondary fluid pathway 252. For instance, the puff sensor 258 may be a pressure-based sensor that detects a pressure gradient caused by a user inhaling from the vaporization device 200. A secondary pressure gradient may be created across the secondary fluid pathway 252.

The secondary pressure gradient may draw a volume of ambient air 236' from the external environment into the ambient air input port 250 that is separate from the volume of ambient air 236 drawn into the heating chamber 214. In response to detecting the ambient air 236', the puff sensor 258 may transmit a puff signal to the control circuit 230. The control circuit 230 may control the flow of the electric current from the battery 228 to the conductive heating element 226 in response to signals from the puff sensor 258.

For example, the puff sensor 258 may detect a user inhalation. The control circuit 230 may then activate the heating element 226 in response to detecting the inhalation in order to generate phyto material vapor.

Providing a separate airflow path 252 for the puff sensor 258 may ensure that the inhalation is detected regardless of the status of the phyto material in the heating chamber 214 (i.e. even if the phyto material prevents or restricts airflow therethrough). Additionally, providing the puff sensor proximate the inhalation aperture 206 as shown may further reduce the time required to identify a user inhalation.

In some embodiments, the volume of ambient air 236' passing through the secondary fluid pathway 252 may trigger the pressure-based puff sensor 258 to monitor the flow rate of the second volume of ambient air 236'. This may be used to monitor the duration and strength of inhalation from a user.

As shown in FIG. 6, the vaporization device 200 can also include a first battery contact 266 and a second battery contact 268. The first battery contact 266 and the second battery contact 268 may be electrically coupled to the control circuit 230.

The contacts 266/268 may be engageable with corresponding contacts of a battery recharging hub. The recharging hub may be connected to an external power source or may contain a battery of its own, or both. The recharging hub may provide electrical energy from the recharging contacts to the battery 230 via battery contacts 266, 268.

As shown, the battery contacts 266, 268 may protrude from the housing 202. Alternatively, the battery contacts 266, 268 may be providing flush with the housing 202.

Alternatively, charging ports may be provided on the vaporization device 200. For instance, the vaporization device 200 may incorporate a micro-USB or USB-C charging port to allow the energy storage member 228 to be recharged.

Optionally, a recharging unit may also be provided that corresponds to the vaporization device 100/200. The recharging may include a secondary housing within which the vaporization device can be positioned for charging. For instance, an example of a recharging unit that may be used in embodiments herein is described in further detail in U.S. patent application Ser. No. 14/829,660 the entirety of which is incorporated herein by reference.

Figure 7:
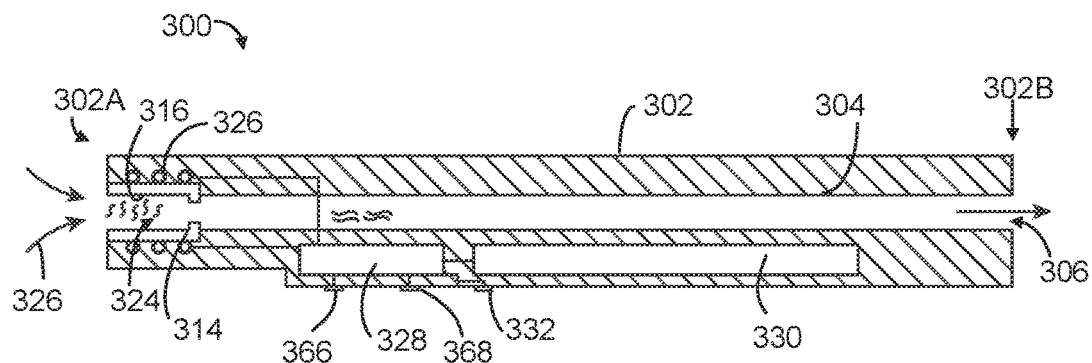
FIG. 7 is a cut-away side view of another example vaporization device, in accordance with an embodiment.

FIG. 7 illustrates another example vaporization device 300 in accordance with an embodiment. Elements having similar structure and/or performing similar function as those in the example vaporization device 100 in FIGS. 1 to 2 are numbered similarly, with the reference numerals incremented by 200.

Vaporization device 300 is an example of a vaporization device employing a heating element 336 coupled to the chamber wall 316. As shown in FIG. 7, a conductive heating element 336 is positioned around the chamber wall 316 of the heating chamber 314. In some cases, the heating element 336 may be embedded within the chamber wall 316. The conductive heating element 336 is configured to heat the internal cavity 324 of the heating chamber 314 by heating the chamber wall 316. The chamber wall 316 can then transfer the heat to phyto material positioned within the heating chamber 314. This may provide the heating chamber 314 with a simplified structure that may be more easily cleaned.

Figure 8:
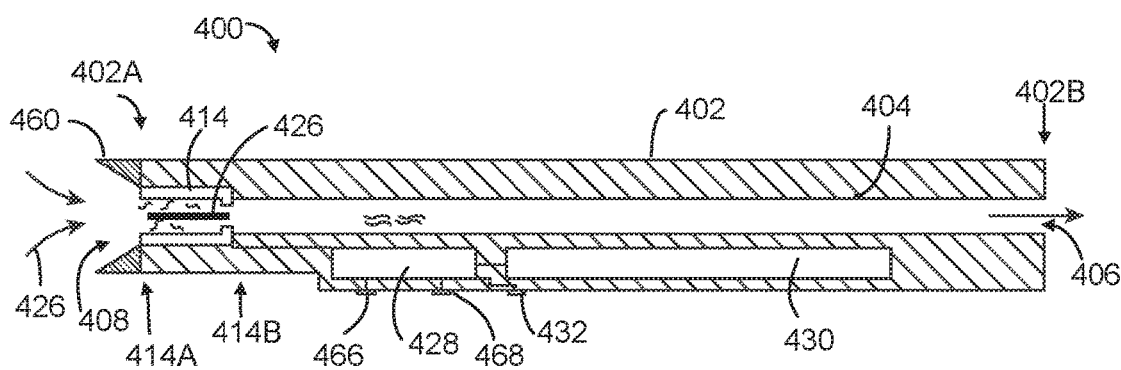
FIG. 8 is a cut-away side view of another example vaporization device, in accordance with an embodiment.

FIG. 8 illustrates another example vaporization device 400 in accordance with an embodiment. Elements having similar structure and/or performing similar function as those in the example vaporization device 100 in FIGS. 1 to 2 are numbered similarly, with the reference numerals incremented by 300.

The vaporization device 400 is an example of a vaporization device employing a cylindrical heating chamber 414. The cylindrical heating chamber 414 can be positioned within the open housing end 408 such that the heating chamber first end 414A is aligned with the housing first end 402A and the heating second chamber end 414B is displaced from the housing first end 402A toward the housing second end 402B.

The vaporization device 400 may also be used as a phyto material preparation device. As shown in FIG. 8, the heating first chamber end 414A has a sharpened or pointed outer edge 460. The pointed edge 460 may be usable to cut or separate phyto material that is to be loaded into the heating chamber 414.

To prepare phyto material for loading, a user can hold the vaporization device 400 like a wand and position the pointed edge 460 to contact the phyto material. The edge 460 can be sharpened so that when pressed against the phyto material, the phyto material may tend to separate.

In some embodiments, the pointed edge 460 may be removably coupled to the heating chamber first end 414A. For example, the pointed edge 460 may be removed for sharpening or when it is otherwise not needed (e.g. when phyto material is loaded in the heating chamber 414).

FIG. 9 illustrates another example vaporization device 500 in accordance with an embodiment. Elements having similar structure and/or performing similar function as those in the example vaporization device 100 in FIGS. 1 to 2 are numbered similarly, with the reference numerals incremented by 400.

The vaporization device 500 includes a cylindrical heating chamber 514. A heating element 526 extends into the heating chamber 514. In the example of FIG. 9, the heating element 526 is a cylindrical rod-shaped heating element 526.

As shown in FIG. 9, the rod-shaped heating element 526 is aligned centrally within the internal cavity 524 of the heating chamber 514. That is, a heating chamber central axis 562 and a heating element central axis 564 are co-axial. As a result, the rod-shaped heating element is equally spaced from the chamber ball 516. In the illustrated example, the rod-shaped heating element 526 can be configured to radiate heat outwardly toward the chamber wall 516.

Figure 11:
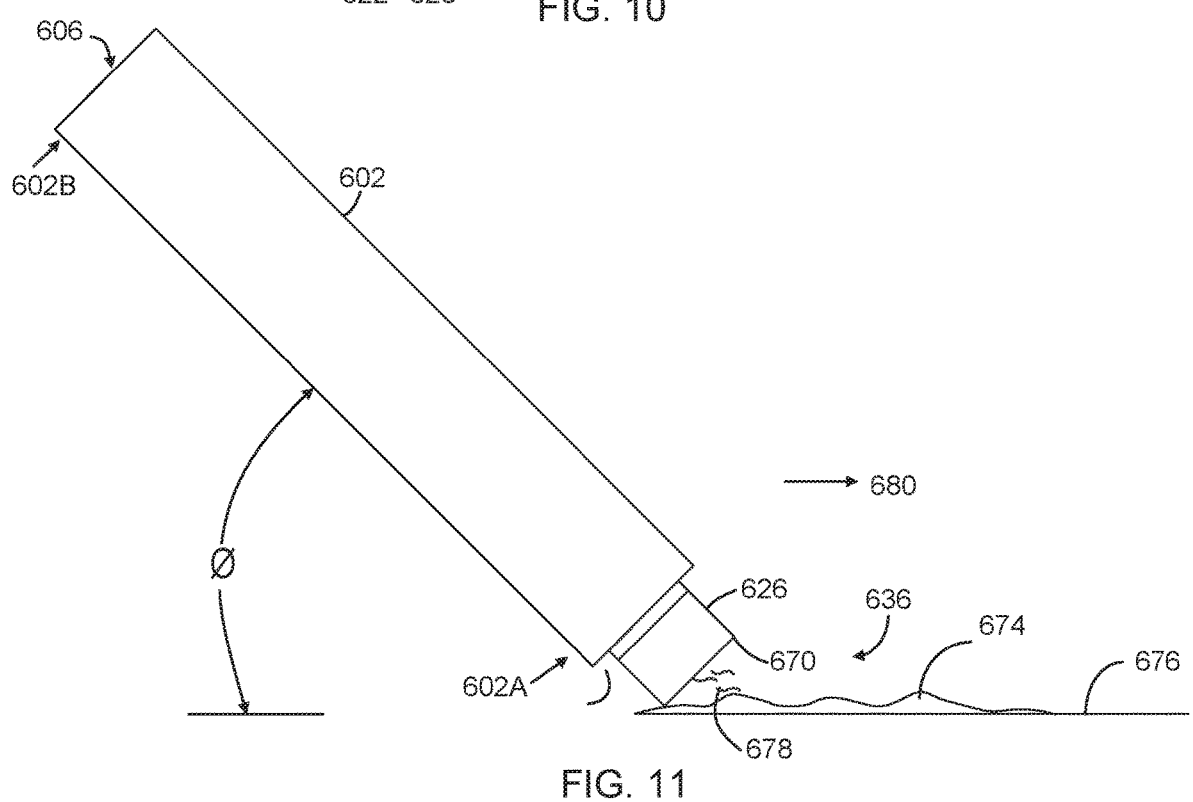
FIG. 11 is a side view of the example vaporization device of FIG. 10 showing the cylindrical conductive heating element in contact with phyto material provided on a surface.
Figure 12:
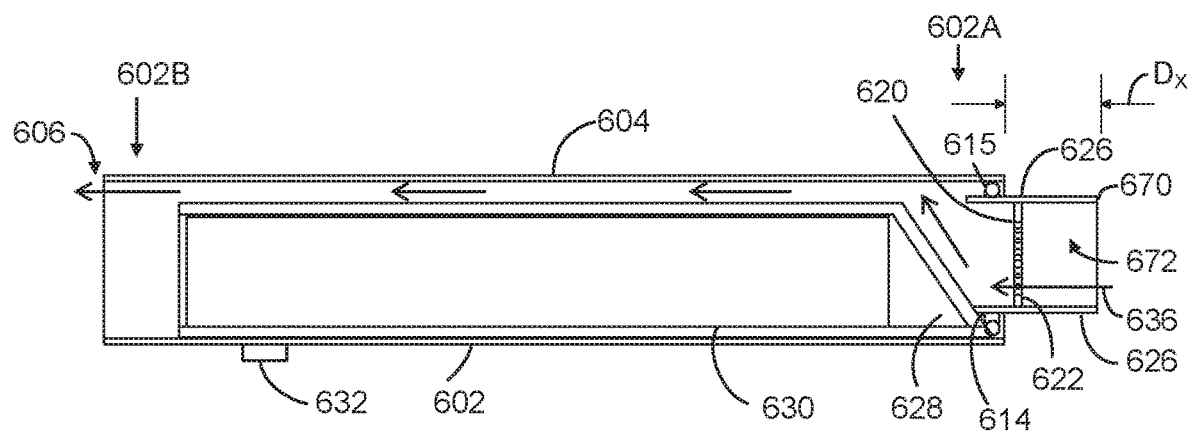
FIG. 12 is a cut-away side view of the example vaporization device of FIG. 10.

FIGS. 10-12 illustrate another example vaporization device 600 in accordance with an embodiment. Elements having similar structure and/or performing similar function as those in the example vaporization device 100 in FIGS. 1 to 2 are numbered similarly, with the reference numerals incremented by 500.

Vaporization device 600 includes a heating chamber 614. The heating chamber 614 defines a cylindrical heating element 626. The heating element 626 may include electrical coils 615 positioned at a second end 614A of the heating chamber 614. The electrical coils 615 may be positioned to contact the chamber wall 616. Alternatively, the coils may be embedded within the chamber wall 616. The coils may operate to heat the chamber wall 616 to provide the heating element 626.

In the illustrated example, an outer edge 670 of the cylindrical heating element 626 protrudes a distance $D_x$ from the first housing end 602A. As shown in FIG. 10, an interior 672 of the heating chamber 614 is fluid communication with a fluid pathway that extends from the first end 602A of the housing 602 to an inhalation aperture 606 positioned at the second end 602B of the housing 602. The closed end 620 of the heating chamber 614 can include one or more vents or vapor inlets 622 coupling the heating chamber 614 to the fluid pathway.

In use, the outer edge 670 of heating element 626 can be heated to a predetermined vaporization temperature. The outer edge 670 may be positioned in contact with a phyto material or phyto material extract 674 to vaporize the phyto material. For instance, phyto material may be positioned on a surface 676 (see FIG. 11) and the vaporization device 600 may be moved into contact with the phyto material to instigate vaporization. Thus, the phyto material need not be loaded into the vaporization device 600.

Vaporization device 600 may be used to vaporize phyto material extract that is not positioned within the heating chamber 614. Rather, the outer edge 670 of the heating element 626 may be placed in contact with external phyto material extract to induce vaporization. The heating chamber 614 may then act as an inhalation chamber that captures the vapor emitted and directs it to the fluid pathway and through to the inhalation aperture 606.

Vaporizing phyto material extract while external to vaporization device 600 may prevent the extract from becoming clogged in the heating chamber 614 and/or vents 622. This may reduce the amount of cleaning required for vaporization device 600 and may prolong the usable life of the vaporization device 600.

As shown in the example of FIG. 11, the vaporization device 600 may be used in a manner akin to a straw. A user may position the inhalation aperture 606 in their mouth and the outer edge 670 of the cylindrical heating element 626 on the phyto material 674 provided on the surface 676. The vaporization device 600 can be orientated at an angle θ to the surface in order to permit ambient air 636 from the external environment to be drawn into the cylindrical heating element 626. Preferably, the vaporization device 600 may be held at an angle between 40 and 90 degrees measured from the surface 676 to encourage the vapor to rise into the vaporization device 600.

The battery 628 can provide electric current to the coils 615 to heat the cylindrical heating element 626. For instance, the battery 628 may provide current in response to activation of the user-activated switch 632 and/or detection of airflow using an airflow or puff sensor as described herein above.

The cylindrical heating element 626 can heat the phyto material 674 to a predefined vaporization temperature. In the illustrated example, the outer edge 670 of the cylindrical heating element 626 contacts and heats the phyto material 674 provided on the surface 676. When the temperature of the phyto material exceeds its vaporization temperature, the phyto material 674 emits a vapor 678. A user may then inhale through the vaporization device 600 as described herein above.

During inhalation, the user may slide the vaporization device 600 along the surface 676 (e.g. in a direction 680). This may allow the outer edge 670 of the cylindrical heating element 626 to come into contact with and vaporize a given quantity of phyto material 674. When compared to phyto material that may be densely packed into an internal cavity of a heating chamber, the heating element 626 may come into more direct contact with the phyto material 674. Accordingly, the phyto material 674 may be more easily and consistently heated to its specific vaporization temperature.

Figure 13:
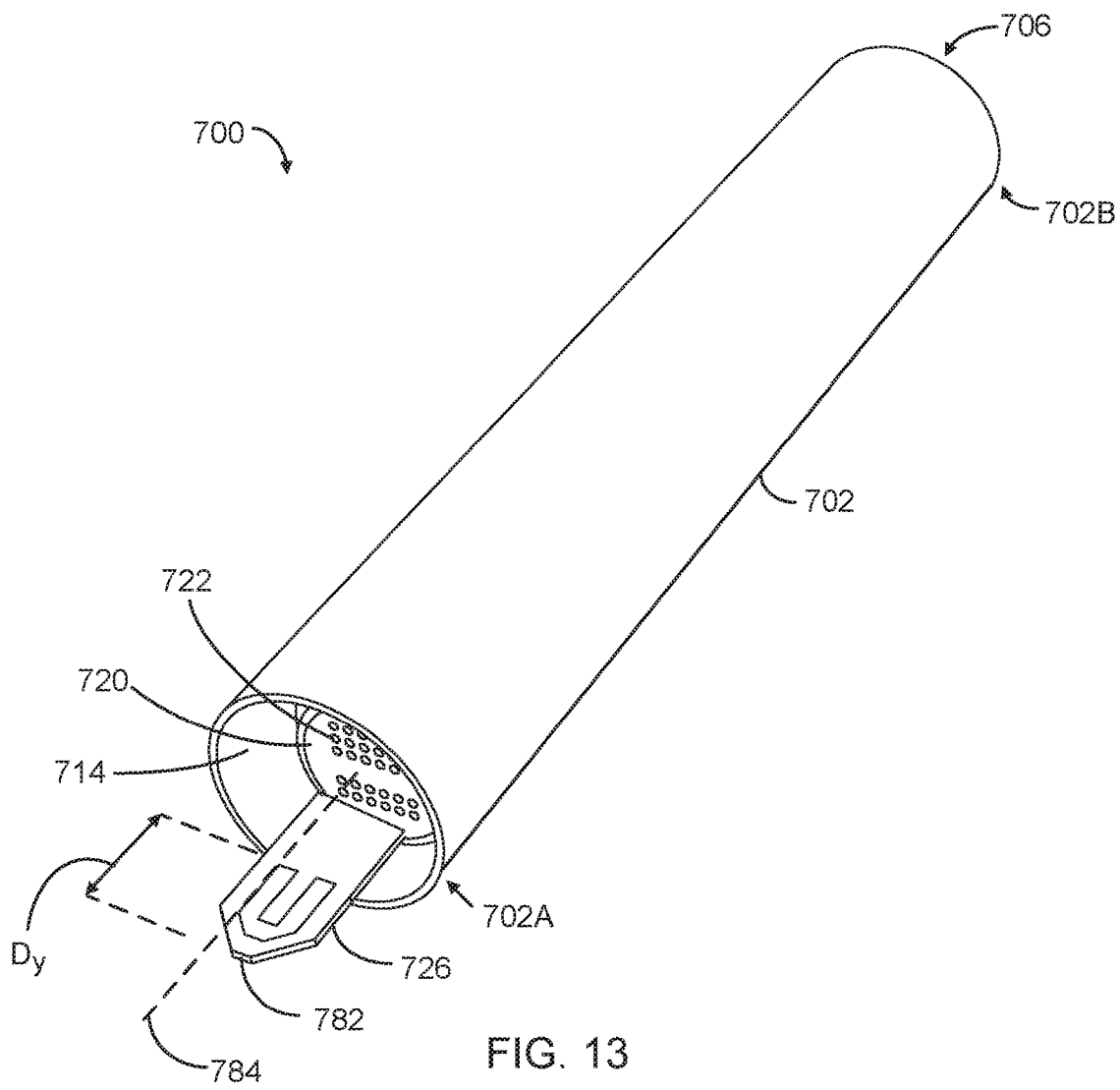
FIG. 13 is a perspective view of another example vaporization device, in accordance with an embodiment.
Figure 14:
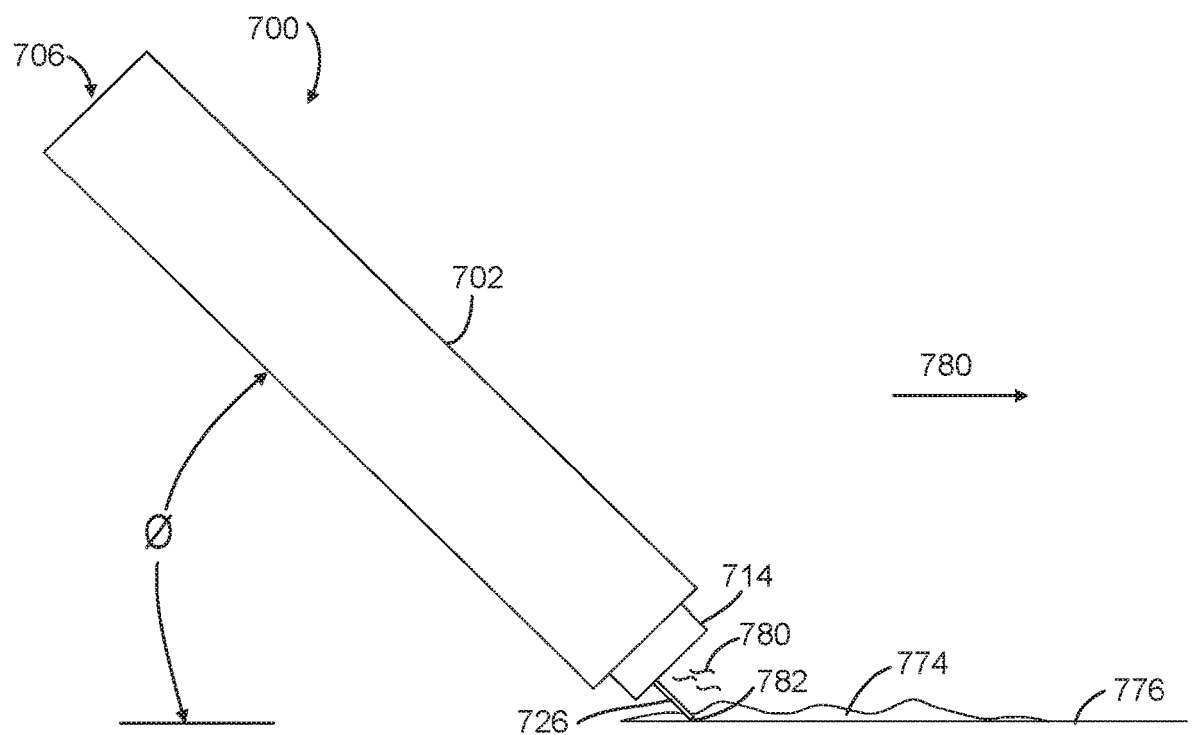
FIG. 14 is a side view of the example vaporization device of FIG. 13 showing an example heating element in contact with phyto material, in accordance with an embodiment.

FIGS. 13 and 14 illustrate another example vaporization device 700 in accordance with an embodiment. Elements having similar structure and/or performing similar function as those in the example vaporization device 100 in FIGS. 1 to 2 are numbered similarly, with the reference numerals incremented by 600.

Vaporization device 700 is another example vaporization device that may be usable without loading phyto material into a heating chamber. Vaporization device includes a heating element 726 that extends outward from the housing 702. As shown, a flat plate heating element 726 is coupled to the first end 702A of the housing 702. The heating element 726 extends passed the housing first end 702A such that a portion of the heating element 726 protrudes from the housing first ends 702A.

In the illustrated example, an outer tip 782 of the flat plate ceramic heating element 726 extends a distance $D_y$ from the first housing end 602A. As shown in FIG. 13, the internal cavity 724 of the heating chamber 714 can be in fluid communication with fluid pathway 704 through one or more vents 722 on the closed chamber wall 720. Vaporization device 700 is another example of a vaporization device in which the heating chamber 714 may operate as an inhalation or vapor gather chamber when the heating element 726 vaporizes phyto material extract external to vaporization device 700.

In use, the outer tip 782 of heating element 726 may be positioned to contact with phyto material 774 provided on a surface 776 (see e.g. FIG. 14). The vaporization device 700 may be used to vaporize the phyto material 774 in a similar manner as the vaporization device 600 illustrated in FIGS. 10 to 12.

As shown in FIGS. 13 and 14, the heating element 726 can be offset from a central axis 784 of the cylindrical heating chamber 714. For instance, the heating element 726 may be offset on the opposite of the central axis from the inhalation aperture 706. By positioning the inhalation aperture 706 offset to a first side of the central axis, a user may be encouraged to use the vaporization device with the inhalation aperture 706 at a raised or upper position. Thus, the heating element 726 may be positioned proximate the surface on which the phyto material 774 is positioned. By offsetting the heating element 726 from the vapor inlets, the vapor emitted from the phyto material 774 may be encouraged to flow upwards into the vapor inlets 722.

The vaporization devices shown in FIGS. 10-15 may also be usable as a wand that can be used to poke, stir or to heat phyto material or phyto material extract disposed within bowl or other non-planar surface.

Figure 15:
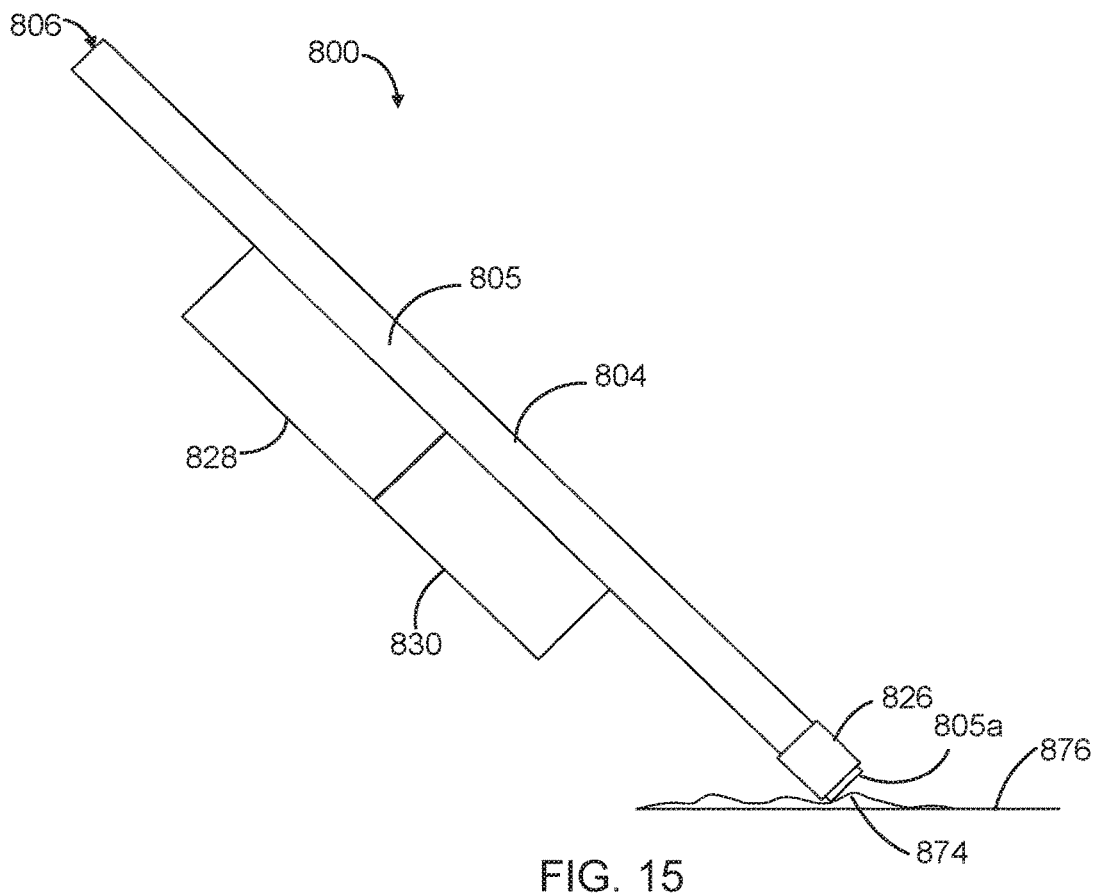
FIG. 15 is a side view of another example vaporization device showing another example heating element in contact with phyto material, in accordance with an embodiment.

FIG. 15 illustrates another example vaporization device 800 in accordance with an embodiment. Elements having similar structure and/or performing similar function as those in the example vaporization device 100 in FIGS. 1 to 2 are numbered similarly, with the reference numerals incremented by 700.

The example vaporization device 800 is shown with its housing removed. As shown in FIG. 15, the vaporization device 800 may include a tube 805 enclosing a continuous fluid pathway 804. An energy storage member 828 and control circuit 830 can be mounted to one side of the fluid pathway 804.

The fluid pathway 804 can extend between an inhalation aperture 806 and a heating element 826. The heating element 826 may be mounted at, or proximate to, the first end 805a of the tube 805. The heating element 826 can heat the tube 805 which in turn can be brought into contact with the phyto material 874. The tube 805, thus heated may be used in a manner analogous to those of vaporization devices 600 and 700 to vaporize phyto material 874 positioned on a surface 876.

In some cases, the heating element 826 may be slightly offset from the first end 805a. This may ensure that the heating element 826 does not directly contact the phyto material 874 being vaporized. Rather, the heating element 826 heats the glass tube 802 through conductive heating and then the tube 805 heats the phyto material extract when placed in contact therewith.

The tube 805 may be manufactured of glass. For example, the tube 805 may be manufactured using a fused quartz glass or a borosilicate glass.

The tube 805, heating element 826, energy storage member 828 and control circuit 830 can be enclosed within a housing such as those described herein above. The first end 805a of the tube 805 may protrude from the housing to allow the heated tube 805 to contact phyto material extract directly. Accordingly, the vaporization device may include a heating chamber operable as a vapor gathering chamber in such cases.

Figure 16:
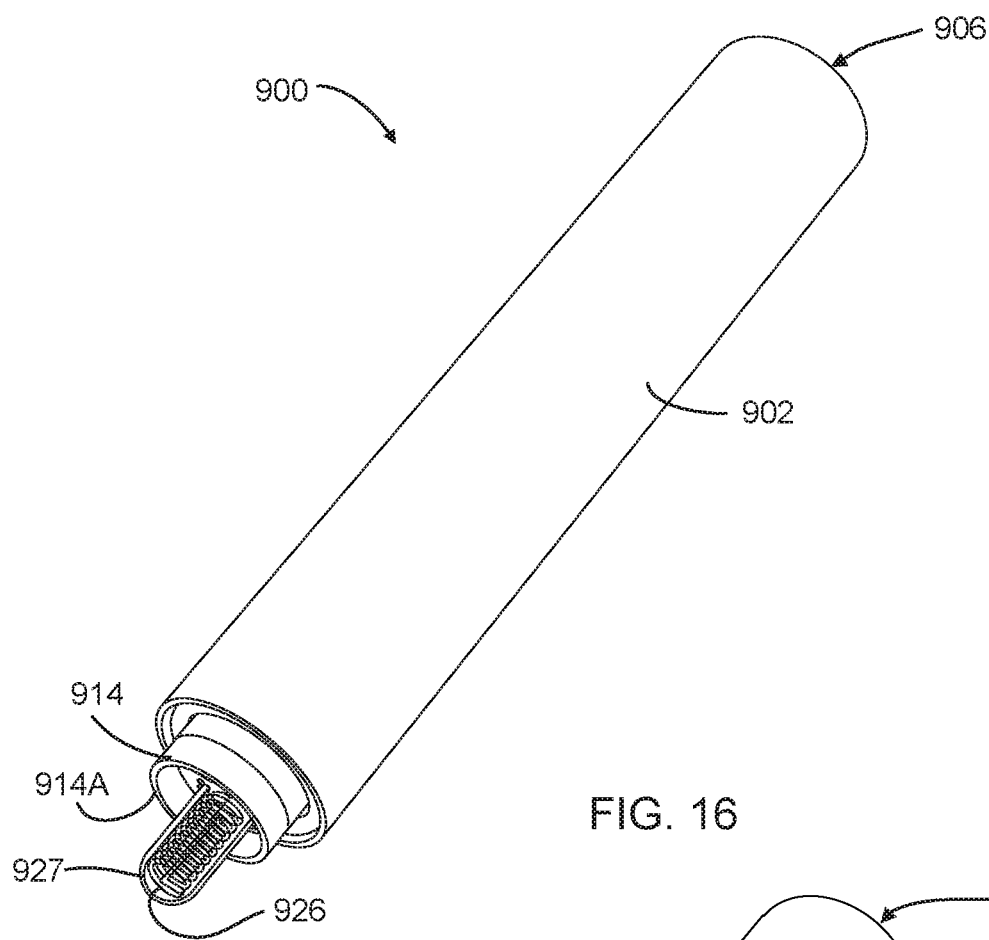
FIG. 16 is a perspective view of another example vaporization device, in accordance with an embodiment.

FIG. 16 illustrates another example vaporization device 900 in accordance with an embodiment. Elements having similar structure and/or performing similar function as those in the example vaporization device 100 in FIGS. 1 to 2 are numbered similarly, with the reference numerals incremented by 800.

As shown in FIG. 16, vaporization device 900 includes a housing 902 that extends from an inhalation aperture 906 to a heating chamber 914. A heating element 926 protrudes from the first end 914A of the heating chamber 914. In vaporization device 900, the heating chamber 914 may operate as a vapor gathering chamber when heating element 926 is used to vaporize phyto material or extract external to vaporization device 900.

The heating element 926 includes an electric coil enclosed within a heating element housing 927. The coil can be a resistive wire coil operable to radiate heat outwards towards the heating element housing 927. The heating element housing 927 can then contact and vaporize phyto material extract.

As explained above, using a wire coil heater may provide for more rapid heating times. Accordingly, in some embodiments, the heating element 926 may be activated in response to the detection of a user inhaling from inhalation aperture 906 (or an adjacent secondary inhalation aperture).

The heating element housing 927 may facilitate cleaning of the vaporization device 900. For instance, the heating element housing 927 may be manufactured using glass or another relatively easily cleanable material. Thus, the heating element housing 927 may be wiped clean by a user after use, while protecting the coil heater from becoming dirty or clogged.

Figure 17:
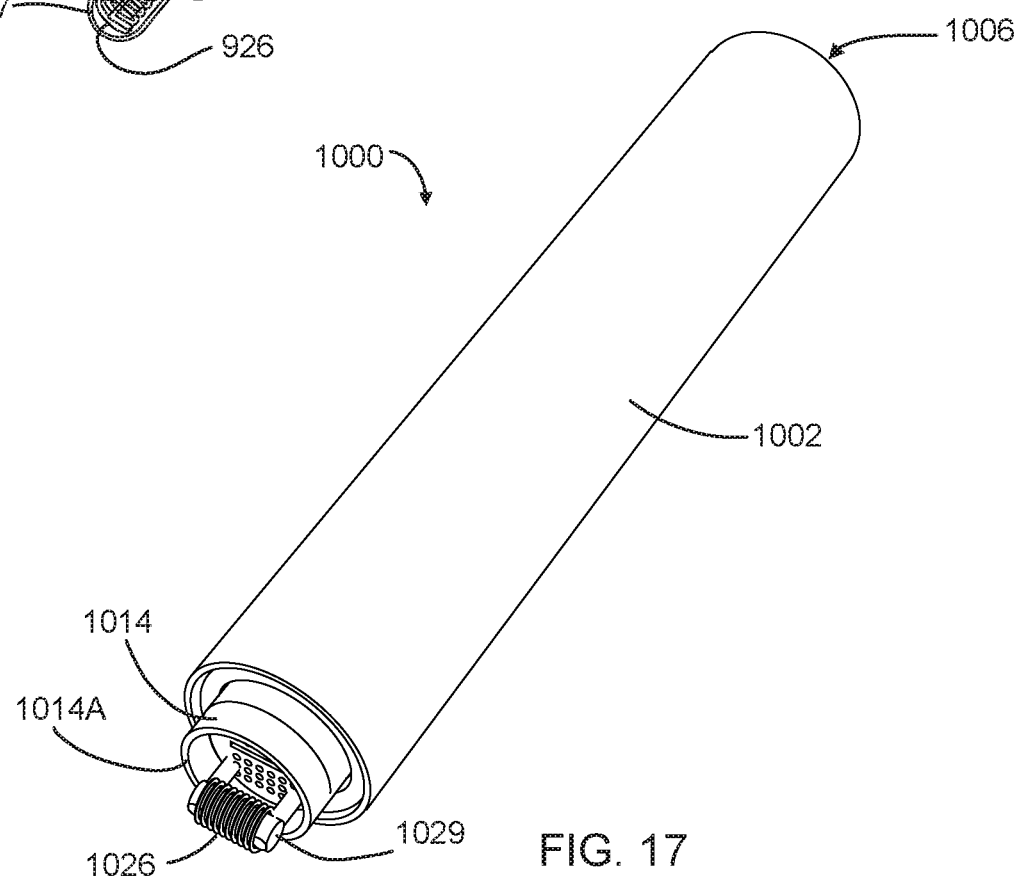
FIG. 17 is a perspective view of another example vaporization device, in accordance with an embodiment.

FIG. 17 illustrates another example vaporization device 1000 in accordance with an embodiment. Elements having similar structure and/or performing similar function as those in the example vaporization device 100 in FIGS. 1 to 2 are numbered similarly, with the reference numerals incremented by 900.

As shown in FIG. 17, vaporization device 1000 includes a housing 1002 that extends from an inhalation aperture 1006 to a heating chamber 1014. A heating element 1026 protrudes from the first end 1014A of the heating chamber 1014. In vaporization device 1000, the heating chamber 1014 may operate as a vapor gathering chamber when the protruding heating element 1026 is used to heat phyto material or extract external to the heating chamber 1014.

The heating element 1026 includes an electric coil mounted on a heating element support 1029. For instance, the heating element support 1029 may be a quartz or ceramic rod extending from the second end of the heating chamber 1014.

As with heating element 926, the coil can be a resistive wire coil operable to radiate heat. The heating element 1026 may be exposed to directly contact phyto material extract. Accordingly, the heating element 1026 may contact and vaporize phyto material extract directly.

As explained above, using a wire coil heater may provide for more rapid heating times. Accordingly, in some embodiments, the heating element 1026 may be activated in response to the detection of a user inhaling from inhalation aperture 1006 (or an adjacent secondary inhalation aperture). Providing an exposed heating element 1026 that can directly contact the phyto material or extract may further reduce the ramp-up time to achieve the vaporization temperature.

In some embodiments, the heating element may be detachably attached to the vaporization device. This may facilitate cleaning of the heating element, particularly in embodiments in which the heating element contacts phyto material or extract directly (such as those shown in FIGS. 1, 6, 8-9, 13, 14, 16, and 17 for example). This may also facilitate replacement of the heating elements in case of damage.

In some embodiments, the vaporization devices may be convertible between an extract vaporization device and a phyto material vaporization device. For example, the vaporization devices 600 and 800 may be used to vaporize phyto material or phyto material extract by adjusting the predetermined vaporization temperature to a suitable temperature. Additionally, the vaporization devices 600/800 may vaporize external phyto material extract (or phyto material), while also enabling phyto material (or extract) to be positioned within the heating chamber for vaporization.

In some embodiments, the vaporization devices may include separate heating elements for different operational modes. For instance, vaporization devices 700, 900 and 1000 may include a secondary heating element positioned to contact the chamber wall of the heating chamber. This may allow the vaporization devices 700, 900, and 1000 to vaporize phyto material or extract positioned within the heating chamber even if the protruding heating element is removed.

As used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A vaporization device comprising:
 a) a housing extending axially between a first housing end and a second housing end;
 b) a fluid pathway extending through the housing between the first housing end and the second housing end;
 c) an inhalation aperture fluidly coupled to the fluid pathway, the inhalation aperture positioned at the second housing end;
 d) a heating element that is heatable to at least one predetermined vaporization temperature, wherein the heating element comprises a protruding portion, wherein the protruding portion protrudes from the first housing end thereby enabling the protruding portion to contact phyto material external to the housing, wherein in use the predetermined vaporization temperature is selected to vaporize phyto material proximate the protruding portion of the heating element whereby a phyto material vapor is emitted;

e) an energy storage member disposed within the housing and electrically coupled to the heating element; and f) a control circuit disposed within the housing and electrically coupled to the energy storage member, the control circuit having a user-activated switch operable to control a flow of electric current from the energy storage member to the heating element, wherein, in response to a user inhalation at the inhalation aperture, a pressure gradient is created across the fluid pathway that draws ambient air from the external environment into the fluid pathway and the ambient air mixes with the phyto material vapor, and the mixed phyto material vapor and air are drawn through the fluid pathway to the inhalation aperture.

2. The vaporization device of claim 1, wherein an inner portion of the fluid pathway comprises a thermally conductive liner.

3. The vaporization device of claim 1, wherein the user-activated switch is a mechanical switch.

4. The vaporization device of claim 1, further comprising:

a) a secondary fluid pathway extending between an ambient air input port and a secondary inhalation aperture, wherein the secondary inhalation aperture and the inhalation aperture are adjacent one another and are formed as a joint inhalation aperture at the second housing end, the secondary fluid pathway having a puff sensor therein configured to detect a flow rate within the secondary fluid pathway, wherein a primary pressure gradient is created across the fluid pathway and a secondary pressure gradient is created across the secondary fluid pathway in response to the user inhalation, the primary pressure gradient drawing a first volume of ambient air from the external environment into the fluid pathway and the secondary pressure gradient drawing a second volume of ambient air from the external environmental into the air input port, and the second volume of ambient air triggers the puff sensor to detect the flow rate of the second volume of ambient air and send a puff signal to the control circuit to adjust the flow of the electric current from the energy storage member to the heating element based on the detected flow rate.

5. The vaporization device of claim 1, wherein a central axis of the housing is offset from a central axis of the fluid pathway.

6. The vaporization device of claim 1, further comprising a first contact and a second contact, the first contact and the second contact being electrically coupled to the control circuit and protruding from the housing, wherein the first contact and the second contact are respectively engageable with a first energy storage member recharging contact and a second energy storage member recharging contact of a recharging hub to provide electrical energy from the recharging port to the energy storage member.

7. The vaporization device of claim 1 comprising a heating chamber proximate to the housing first end, the heating chamber in fluid communication with the fluid pathway, wherein the heating chamber defines a phyto material receiving area in which phyto material is positionable to enable vaporization, the heating chamber having a heating chamber first end, a heating chamber second end and a heating chamber wall that extends between the heating chamber first end and the heating chamber second end, wherein the heating element is one of positioned to contact the chamber wall and integrated with the chamber wall, wherein the outer end of the heating chamber has a pointed peripheral edge operable to cut phyto material when pressed against it.

8. The vaporization device of claim 5, wherein the heating element comprises a blade shaped heating element offset from the central axis, the blade configured to radiate heat outwardly.

9. The vaporization device of claim 1, wherein the heating element is a rod-shaped heating element aligned centrally within an internal cavity of the heating chamber, the rod-shaped heating element configured to radiate heat outwardly.

10. The vaporization device of claim 7, wherein the heating chamber comprises a closed chamber end wall at the first end and the heating chamber is in fluid communication with the fluid pathway through one or more vents formed in the closed chamber end wall.

11. The vaporization device of claim 1, wherein:

the heating element comprises a heating element housing and an electric coil enclosed within the heating element housing;

the electric coil comprising a resistive wire coil operable to radiate heat outwards towards the heating element housing wherein the heating element housing is usable to contact and vaporize the phyto material.

12. The vaporization device of claim 1, wherein the heating element is detachably attached to the vaporization device proximate the housing first end.

13. The vaporization device of claim 1, wherein the heating element is a flat plate ceramic heating element.

14. The vaporization device of claim 13, further comprising a central axis extending axially between the first housing end and the second housing end;

wherein the flat plate ceramic heating element is offset from the central axis.

15. The vaporization device of claim 1, wherein the heating element is a cylindrical heating element.

16. The vaporization device of claim 1 further comprising a heating element cover, wherein the heating element cover comprises an adjustable sliding member that is adjustable between a closed position and an open position, wherein in the closed position the sliding member covers the heating element and in the open position the sliding member exposes the heating element for use.

17. A vaporization device comprising:

a) a cylindrical housing extending axially between a first housing end and a second housing end;

b) a fluid pathway extending through the housing between the first housing end and the second housing end;

c) an inhalation aperture at the second housing end, the inhalation aperture fluidly coupled to the fluid pathway;

d) a releasable heating element that is heatable to at least one predetermined vaporization temperature, wherein the heating element comprises a protruding portion, wherein the protruding portion protrudes from the first housing end thereby enabling the protruding portion to contact phyto material external to the housing, wherein in use the predetermined vaporization temperature is selected to vaporize phyto material proximate the protruding portion of the heating element whereby a phyto material vapor is emitted, e) an energy storage member at least partially disposed within the housing and electrically coupled to the heating element; and f) a control circuit at least partially disposed within the housing and electrically coupled to the energy storage member, the control circuit having a user-activated switch operable to control a flow of electric current from the energy storage member to the heating element, wherein in response to a user inhalation at the inhalation aperture, a pressure gradient is created across the fluid pathway that draws ambient air from the external environment into the fluid pathway and the ambient air mixes with the phyto material vapor, and the mixed phyto material vapor and air are drawn through the fluid pathway to the inhalation aperture.

18. The vaporization device of claim 1, wherein the heating element protruding portion defines an outer edge of the heating element and the outer edge of the heating element may be placed in contact with external phyto material extract to induce vaporization.

19. The vaporization device of claim 1, wherein the vaporization device comprises a glass tube enclosing the fluid pathway, wherein a first tube end of the glass tube defines the protruding portion of the heating element.

* * * * *